US009370361B2

(12) United States Patent
Viola et al.

(10) Patent No.: US 9,370,361 B2
(45) Date of Patent: Jun. 21, 2016

(54) SURGICAL STAPLER WITH TIMER AND FEEDBACK DISPLAY

(71) Applicant: COVIDIEN LP, Mansfield, MA (US)

(72) Inventors: Frank J. Viola, Sandy Hook, CT (US); Gregg Krehel, Newtown, CT (US); Michael A. Soltz, North Haven, CT (US); Robert J. DeSantis, Redding, CT (US); Henry E. Holsten, Covington, GA (US); Russell Heinrich, Madison, CT (US)

(73) Assignee: Covidien LP, Mansfield, MA (US)

( * ) Notice: Subject to any disclaimer, the term of this patent is extended or adjusted under 35 U.S.C. 154(b) by 518 days.

(21) Appl. No.: 13/939,589

(22) Filed: Jul. 11, 2013

(65) Prior Publication Data

US 2013/0292451 A1    Nov. 7, 2013

Related U.S. Application Data

(60) Continuation of application No. 13/407,797, filed on Feb. 29, 2012, now Pat. No. 8,505,802, which is a continuation of application No. 13/277,544, filed on Oct. 20, 2011, now Pat. No. 8,157,150, which is a (Continued)

(51) Int. Cl.
*A61B 17/04* (2006.01)
*A61B 17/068* (2006.01)
(Continued)

(52) U.S. Cl.
CPC .............. *A61B 17/068* (2013.01); *A61B 17/072* (2013.01); *A61B 17/07207* (2013.01);
(Continued)

(58) Field of Classification Search
CPC ............. A61B 17/069; A61B 17/0686; A61B 17/072; A61B 17/07207; A61B 17/115; A61B 2017/07214
USPC ............... 227/19, 175.1, 175.2, 175.3, 176.1, 227/180.1; 606/139, 153, 219
See application file for complete search history.

(56) References Cited

U.S. PATENT DOCUMENTS 37,165 A   12/1862  Gary
3,079,606 A   3/1963  Bobrov et al.
(Continued)

FOREIGN PATENT DOCUMENTS

AU    2008229795 A1    4/2009
CN    101856251 A    10/2010
(Continued)

OTHER PUBLICATIONS

European Search Report No. 13189650.8 dated Sep. 10, 2014.
(Continued)

*Primary Examiner* — Scott A. Smith

(57) ABSTRACT

A surgical apparatus has a clamp and a stapling mechanism. The clamp has a first jaw and a second jaw to clamp on a body tissue at a desired location for a stapling operation. The stapling mechanism is controlled by a trigger handle or a switch assembly. The surgical apparatus has a controller for providing a delay between clamping and actuating of the firing mechanism of the stapling mechanism. The delay provides for a desired amount of time for tissue compression producing a more uniform staple formation. The surgical apparatus also has an indicator. The indicator provides feedback about the status of the stapling mechanism and also displays a time of tissue compression by the clamp.

10 Claims, 15 Drawing Sheets

Related U.S. Application Data continuation of application No. 12/959,421, filed on Dec. 3, 2010, now Pat. No. 8,052,024, which is a continuation of application No. 12/645,144, filed on Dec. 22, 2009, now Pat. No. 7,845,534, which is a continuation of application No. 12/108,916, filed on Apr. 24, 2008, now abandoned, which is a division of application No. 11/446,282, filed on Jun. 2, 2006, now Pat. No. 7,464,847.

(60) Provisional application No. 60/687,406, filed on Jun. 3, 2005, provisional application No. 60/687,244, filed on Jun. 3, 2005.

(51) Int. Cl.
*A61B 17/072* (2006.01)
*A61B 17/12* (2006.01)
*A61B 17/00* (2006.01)
*A61B 17/29* (2006.01)
*A61B 17/32* (2006.01)
*A61B 19/00* (2006.01)

(52) U.S. Cl.
CPC ....... *A61B17/12* (2013.01); *A61B 2017/00115* (2013.01); *A61B 2017/00128* (2013.01); *A61B 2017/00398* (2013.01); *A61B 2017/00734* (2013.01); *A61B 2017/07214* (2013.01); *A61B 2017/2943* (2013.01); *A61B 2017/320052* (2013.01); *A61B 2019/4857* (2013.01)

(56) References Cited

U.S. PATENT DOCUMENTS

| | | |
|---|---|---|
| 3,209,754 A | 10/1965 | Brown |
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,722,685 A | 2/1988 | de Estrada et al. |
| 4,724,839 A | 2/1988 | Bedi |
| 4,805,617 A | 2/1989 | Bedi et al. |
| 4,807,628 A | 2/1989 | Peters et al. |
| 4,823,807 A | 4/1989 | Russell et al. |
| 4,852,558 A | 8/1989 | Outerbridge |
| 4,913,144 A | 4/1990 | DelMedico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girnes |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,301,061 A | 4/1994 | Nakada et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,395,030 A | 3/1995 | Kuramoto et al. |
| 5,395,033 A | 3/1995 | Byrne et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,427,087 A | 6/1995 | Ito et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,527,235 A | 6/1996 | Kuroda et al. |
| 5,529,235 A | 6/1996 | Boiarski et al. |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,558,671 A | 9/1996 | Yates |
| 5,560,532 A | 10/1996 | DeFonzo et al. |

(56) References Cited

U.S. PATENT DOCUMENTS

| | | |
|---|---|---|
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,432 A | 5/1997 | Schulze et al. |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Nenetti et al. |
| 5,735,848 A | 4/1998 | Yates et al. |
| 5,738,474 A | 4/1998 | Blewett |
| 5,755,726 A | 5/1998 | Pratt |
| 5,759,171 A | 6/1998 | Coelho et al. |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A | 8/2000 | Alli et al. |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,239,732 B1 | 5/2001 | Cusey |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,371,909 B1 | 4/2002 | Hoeg et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |

(56) References Cited

U.S. PATENT DOCUMENTS

| | | |
|---|---|---|
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnsude et al. |
| 6,616,821 B2 | 9/2003 | Broadley et al. |
| 6,629,986 B1 | 10/2003 | Ross et al. |
| 6,645,218 B1 | 11/2003 | Cassidy et al. |
| 6,651,669 B1 | 11/2003 | Burnside |
| 6,654,999 B2 | 12/2003 | Stoddard et al. |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B1 | 5/2004 | Esnouf |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| RE39,152 E | 6/2006 | Aust et al. |
| 7,059,508 B2 | 6/2006 | Shelton et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV |
| 7,147,138 B2 | 12/2006 | Shelton, IV |
| 7,172,104 B2 | 2/2007 | Scirica et al. |
| 7,186,966 B2 | 3/2007 | Al-Ali |
| 7,193,519 B2 | 3/2007 | Root et al. |
| 7,217,269 B2 | 5/2007 | El-Galley et al. |
| 7,220,232 B2 | 5/2007 | Suorsa et al. |
| 7,225,964 B2 | 6/2007 | Mastri et al. |
| 7,238,021 B1 | 7/2007 | Johnson |
| 7,240,817 B2 | 7/2007 | Higuchi |
| 7,241,270 B2 | 7/2007 | Jorzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smirh et al. |
| 7,407,078 B2 | 8/2008 | Shelton, IV et al. |
| 7,422,136 B1 | 9/2008 | Marczyk |
| 7,464,846 B2 | 12/2008 | Shelton, IV et al. |
| 7,464,847 B2 | 12/2008 | Viola et al. |
| 7,481,824 B2 | 1/2009 | Boudreaux et al. |
| 7,565,993 B2 | 7/2009 | Milliman et al. |
| 7,575,144 B2 | 8/2009 | Ortiz et al. |
| 7,699,835 B2 | 4/2010 | Lee et al. |
| 7,793,812 B2 | 9/2010 | Moore et al. |
| 7,822,458 B2 | 10/2010 | Webster, III et al. |
| 7,845,534 B2 | 12/2010 | Viola et al. |
| 7,857,185 B2 | 12/2010 | Swayze et al. |
| 7,870,989 B2 | 1/2011 | Viola et al. |
| 7,922,719 B2 | 4/2011 | Ralph et al. |
| 7,954,682 B2 | 6/2011 | Giordano et al. |
| 7,959,051 B2 | 6/2011 | Smith et al. |
| 7,967,179 B2 | 6/2011 | Olson et al. |
| 8,016,178 B2 | 9/2011 | Olson et al. |
| 8,025,199 B2 | 9/2011 | Whitman et al. |
| 8,052,024 B2 | 11/2011 | Viola et al. |
| 8,056,787 B2 | 11/2011 | Boudreaux et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,186,587 B2 | 5/2012 | Zmood et al. |
| 8,235,273 B2 | 8/2012 | Olson et al. |
| 8,272,554 B2 | 9/2012 | Whitman et al. |
| 8,303,581 B2 | 11/2012 | Arts et al. |
| 8,342,379 B2 | 1/2013 | Whitman et al. |
| 8,353,440 B2 | 1/2013 | Whitman et al. |
| 8,365,633 B2 | 2/2013 | Simaan et al. |
| 8,371,492 B2 | 2/2013 | Aranyi et al. |
| 8,424,739 B2 | 4/2013 | Racenet et al. |
| 8,454,585 B2 | 6/2013 | Whitman |
| 8,505,802 B2 | 8/2013 | Viola et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,696,552 B2 | 4/2014 | Whitman |
| 8,708,213 B2 | 4/2014 | Shelton, IV et al. |
| 8,752,749 B2 | 6/2014 | Moore et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,967,443 B2 | 3/2015 | McCuen |
| 8,968,276 B2 * | 3/2015 | Zemlok ............ A61B 17/07207 606/1 |
| 9,016,545 B2 * | 4/2015 | Aranyi ............ A61B 17/07207 227/175.1 |
| 9,216,013 B2 * | 12/2015 | Scirica ............ A61B 17/07207 |
| 9,289,211 B2 * | 3/2016 | Williams ......... A61B 17/07207 |
| 2002/0025891 A1 | 2/2002 | Colosky et al. |
| 2002/0103489 A1 | 8/2002 | Ku |
| 2002/0111641 A1 | 8/2002 | Peterson et al. |
| 2002/0165541 A1 | 11/2002 | Whitman |
| 2003/0038938 A1 | 2/2003 | Jung et al. |
| 2003/0073981 A1 | 4/2003 | Whitman et al. |
| 2003/0114851 A1 | 6/2003 | Truckai et al. |
| 2003/0120306 A1 | 6/2003 | Burbank et al. |
| 2003/0139746 A1 | 7/2003 | Groiso |
| 2004/0094597 A1 | 5/2004 | Whitman et al. |
| 2004/0133189 A1 | 7/2004 | Sakurai |
| 2004/0176751 A1 | 9/2004 | Weitzner et al. |
| 2004/0232199 A1 | 11/2004 | Shelton, IV et al. |
| 2004/0232201 A1 | 11/2004 | Wenchell et al. |

(56) References Cited

U.S. PATENT DOCUMENTS

| | | |
|---|---|---|
| 2005/0006429 A1 | 1/2005 | Wales et al. |
| 2005/0006430 A1 | 1/2005 | Wales |
| 2005/0006431 A1 | 1/2005 | Shelton, IV et al. |
| 2005/0006434 A1 | 1/2005 | Wales et al. |
| 2005/0010235 A1 | 1/2005 | VanDusseldorp |
| 2005/0023324 A1 | 2/2005 | Doll et al. |
| 2005/0067458 A1 | 3/2005 | Swayze et al. |
| 2005/0070925 A1 | 3/2005 | Shelton, IV et al. |
| 2005/0070958 A1 | 3/2005 | Swayze et al. |
| 2005/0072827 A1 | 4/2005 | Mollenauer |
| 2005/0131390 A1 | 6/2005 | Heinrich et al. |
| 2005/0131442 A1 | 6/2005 | Yachia et al. |
| 2005/0139636 A1 | 6/2005 | Schwemberger et al. |
| 2005/0145674 A1 | 7/2005 | Sonnenschein et al. |
| 2005/0177176 A1 | 8/2005 | Gerbi et al. |
| 2005/0178813 A1 | 8/2005 | Swayze et al. |
| 2005/0187576 A1 | 8/2005 | Whitman et al. |
| 2005/0192609 A1 | 9/2005 | Whitman et al. |
| 2005/0228341 A1 | 10/2005 | Edgerley |
| 2005/0247753 A1 | 11/2005 | Kelly et al. |
| 2006/0000867 A1 | 1/2006 | Shelton, IV et al. |
| 2006/0022014 A1 | 2/2006 | Shelton, IV |
| 2006/0022015 A1 | 2/2006 | Shelton, IV |
| 2006/0097025 A1 | 5/2006 | Milliman et al. |
| 2006/0151567 A1 | 7/2006 | Roy |
| 2006/0175375 A1 | 8/2006 | Shelton, IV |
| 2006/0278680 A1 | 12/2006 | Viola et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0029364 A1 | 2/2007 | Kruszynski et al. |
| 2007/0039995 A1 | 2/2007 | Schwemberger et al. |
| 2007/0039996 A1 | 2/2007 | Mather et al. |
| 2007/0039997 A1 | 2/2007 | Mather et al. |
| 2007/0084896 A1 | 4/2007 | Doll et al. |
| 2007/0084897 A1 | 4/2007 | Shelton, IV et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0125826 A1 | 6/2007 | Shelton, IV |
| 2007/0152014 A1 | 7/2007 | Gillum et al. |
| 2007/0158385 A1 | 7/2007 | Hueil et al. |
| 2007/0175947 A1 | 8/2007 | Ortiz et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV |
| 2007/0175953 A1 | 8/2007 | Shelton, IV |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV |
| 2007/0175958 A1 | 8/2007 | Shelton, IV |
| 2007/0175959 A1 | 8/2007 | Shelton, IV |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0187453 A1 | 8/2007 | Smith et al. |
| 2007/0219563 A1 | 9/2007 | Voegele |
| 2007/0265640 A1 | 11/2007 | Kortenbach et al. |
| 2007/0278277 A1 | 12/2007 | Wixey et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0169329 A1 | 7/2008 | Shelton et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0308603 A1 | 12/2008 | Shelton et al. |
| 2009/0090763 A1 | 4/2009 | Zemlok et al. |
| 2009/0171147 A1 | 7/2009 | Lee et al. |
| 2010/0069942 A1 | 3/2010 | Shelton, IV |
| 2011/0006101 A1 | 1/2011 | Hall et al. |
| 2011/0017801 A1 | 1/2011 | Zemlok et al. |
| 2012/0172924 A1 | 7/2012 | Allen, IV |
| 2012/0223121 A1 | 9/2012 | Viola et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |

FOREIGN PATENT DOCUMENTS

| | | |
|---|---|---|
| EP | 0 537 570 | 4/1993 |
| EP | 0 647 431 | 4/1995 |
| EP | 0705571 A1 | 4/1996 |
| EP | 0 738 501 | 10/1996 |
| EP | 1723913 A1 | 11/2006 |
| EP | 1759652 A2 | 3/2007 |
| EP | 1772105 A1 | 4/2007 |
| EP | 1 813 203 | 8/2007 |
| EP | 1908412 A2 | 4/2008 |
| EP | 1917929 A1 | 5/2008 |
| EP | 1943954 A2 | 7/2008 |
| EP | 1943956 A2 | 7/2008 |
| EP | 1952769 A2 | 8/2008 |
| EP | 2044890 A1 | 4/2009 |
| EP | 2090247 A1 | 8/2009 |
| EP | 2100562 A2 | 9/2009 |
| EP | 2245994 A1 | 11/2010 |
| EP | 2272443 A1 | 1/2011 |
| EP | 2316345 A1 | 5/2011 |
| EP | 2324776 A2 | 5/2011 |
| EP | 2377472 A1 | 10/2011 |
| EP | 2462878 A1 | 6/2012 |
| EP | 2676615 A2 | 12/2013 |
| EP | 2815705 A1 | 12/2014 |
| ES | 2333509 A1 | 2/2010 |
| FR | 2861574 A1 | 5/2005 |
| JP | 08-038488 | 2/1996 |
| JP | 2005-125075 A | 5/2005 |
| WO | WO 97/29694 | 8/1997 |
| WO | WO 97/40760 | 11/1997 |
| WO | 99/15086 A1 | 4/1999 |
| WO | WO 99/52489 | 10/1999 |
| WO | 03/030743 A2 | 4/2003 |
| WO | WO 03/026511 | 4/2003 |
| WO | WO 03/030743 | 4/2003 |
| WO | 03065916 A1 | 8/2003 |
| WO | 03090630 A2 | 11/2003 |
| WO | WO 2004/032760 | 4/2004 |
| WO | 2007016290 A2 | 2/2007 |
| WO | WO 2007/030753 | 2/2007 |
| WO | WO 2007/118179 | 10/2007 |
| WO | 2007137304 A2 | 11/2007 |
| WO | 2009/143092 A1 | 11/2009 |

(56) References Cited

FOREIGN PATENT DOCUMENTS

| WO | 2009149234 A1 | 12/2009 |
| WO | 2012040984 A1 | 4/2012 |

OTHER PUBLICATIONS

Extended European Search Report corresponding to EP 08251357.3, completed Sep. 3, 2009 and dated Sep. 29, 2009; (3 pp).
European Search Report corresponding to EP 06 02 6840, dated Apr. 17, 2007.
International Search Report for corresponding PCT Application PCT/US06/21524, dated May 28, 2008.
Detemple, P., "Microtechnology in Modem Health Care", Med Device Technol., 9(9):18-25 (1998).
European Search Report corresponding to EP 08 25 2703.7, dated Oct. 31, 2008.
European Search Report corresponding to EP 08 25 3184.9, dated Feb. 27, 2009.
European Search Report corresponding to EP 08 25 1357.3, dated Sep. 29, 2009.

\* cited by examiner

SURGICAL STAPLER WITH TIMER AND FEEDBACK DISPLAY

CROSS REFERENCE TO RELATED PATENT APPLICATIONS

This patent application is a Continuation application claiming the benefit of and priority to U.S. patent application Ser. No. 13/407,797, filed on Feb. 29, 2012 now U.S. Pat. No. 8,505,902, which is a Continuation application claiming the benefit of and priority to U.S. patent application Ser. No. 13/277,544, filed on Nov. 3, 2011 (now U.S. Pat. No. 8,157, 150), which is a Continuation application claiming the benefit of and priority to U.S. patent application Ser. No. 12/959,421, filed on Dec. 3, 2010 (now U.S. Pat. No. 8,052,024), which is a Continuation application claiming the benefit of and priority to U.S. patent application Ser. No. 12/645,144, filed on Dec. 22, 2009 (now U.S. Pat. No. 7,845,534), which is a Continuation application claiming the benefit of and priority to U.S. patent application Ser. No. 12/108,916, filed on Apr. 24, 2008 (now abandoned), which is a Divisional application claiming the benefit of and priority to U.S. patent application Ser. No. 11/446,282, filed on Jun. 2, 2006 (now U.S. Pat. No. 7,464,847), which claims the benefit of and priority to U.S. Provisional Patent Application Ser. No. 60/687,406 to Viola, et al., filed on Jun. 3, 2005 which is herein incorporated by reference in its entirety.

U.S. patent application Ser. No. 11/446,282, filed on Jun. 2, 2006 (now U.S. Pat. No. 7,464,847) also claims priority to U.S. Provisional Patent Application Ser. No. 60/687,244 to Viola, et al., filed on Jun. 3, 2005 which is also herein incorporated by reference in its entirety.

U.S. patent application Ser. No. 11/446,282, filed on Jun. 2, 2006 (now U.S. Pat. No. 7,464,847), also relates to U.S. patent application Ser. No. 11/446,283, filed on Jun. 2, 2006 (now U.S. Pat. No. 7,461,767), which is herein incorporated by reference in its entirety.

BACKGROUND

1. Technical Field

The present disclosure relates to surgical instruments. More particularly, the present disclosure relates to a surgical stapling device that has a feedback and a timer device. Even more particularly, the present disclosure relates to a surgical stapling device that has a controller to modulate one or more parameters of the surgical stapling device and to provide for compression of tissue. Still even more particularly, the present disclosure relates to a surgical stapling device that may also include a sensory indicator (i.e., visual, audible, tactile) which determines position, time, or other valuable user feedback.

2. Background of the Related Art

Once under pressure from a jawed structure, such as a clamping device, of a surgical stapler, the body tissue will slowly compress. Compression by a clamping device reduces the amount of blood and fluid to the clamped tissue. Without such compression, an uncompressed body tissue remains thicker whereas the compressed body tissue would be thinner, and more compact. Compressing the tissue also causes blood and other fluid to generally traverse from the high pressure or compressed area to another low pressure or adjacent area.

Once released, the fluid due to the visco-elastic property of the tissue will return from the adjacent area to the previously compressed tissue. Some current surgical stapling devices initially compress tissue prior to the introduction of the staple into the body tissue. The amount of time tissue is compressed is currently left to the discretion of the surgeon. The surgeon manually controls the amount of time that the tissue is compressed prior to firing the staples into tissue. It would be therefore desirable to have a surgical stapling device that consistently fires staples after a predetermined amount of compression.

SUMMARY

According to a first embodiment of the present disclosure, there is provided a surgical stapler that has a handle assembly including a stationary handle and a pivotable handle mounted for manipulation through an actuating stroke. In another embodiment, the stapler may have a trigger that is operable to manipulate a cam member through the actuating stroke. The stapler also has an elongated body extending distally from the handle assembly and defining a longitudinal axis and a staple cartridge supported adjacent the distal end of the elongated body and containing a plurality of staples.

The stapler further has an anvil pivotally mounted in relation to the cartridge adjacent the distal end of the elongated body with the anvil having a fastener forming surface thereon and being mounted for pivotal movement in relation to the cartridge between an open position having a distal end spaced from the staple cartridge and a closed position in close cooperative alignment with the staple cartridge. The stapler also has an actuation sled supported within the cartridge. The actuation sled moves to urge the plurality of staples from the cartridge.

The stapler further has a drive assembly including a body having a working end and a cam member supported on the working end. The cam member is positioned to translate relative to the anvil to maintain the anvil in the closed position during firing of the stapler. The trigger or pivotable handle is operatively connected to the drive assembly such that manipulation of the pivotable handle through its actuating stroke effects translation of the cam member relative to the anvil. The stapler also has a channel for supporting the staple cartridge and a controller configured to control the actuation sled supported within the cartridge. The controller delays movement of the actuation sled to urge the plurality of staples from the cartridge for a predetermined time period when the anvil is in the closed position and in cooperative alignment with the staple cartridge.

According to another aspect of the present disclosure, the surgical stapler has a handle assembly including a stationary handle and a trigger configured to manipulate a cam member through an actuating stroke. The stapler also has an elongated body extending distally from the handle assembly and defining a longitudinal axis and a staple cartridge supported adjacent the distal end of the elongated body with staples. The stapler further has an anvil pivotally mounted in relation to the cartridge adjacent the distal end of the elongated body. The anvil has a fastener forming surface thereon and is mounted for pivotal movement in relation to the cartridge between an open position having a distal end spaced from the staple cartridge and a closed position in close cooperative alignment with the staple cartridge.

The stapler also has an actuation sled supported within the cartridge. The actuation sled moves to urge the staples from the cartridge. The drive assembly includes a body having a working end and a cam member supported on the working end. The cam member is positioned to translate relative to the anvil to maintain the anvil in the closed position during firing of the stapler.

The trigger is connected to the drive assembly such that manipulation of the trigger through its actuating stroke effects translation of the cam member relative to the anvil. The stapler also has a channel for supporting the staple cartridge. The stapler also has a controller. The controller is configured to control the actuation sled supported within the cartridge. The controller delays the actuation sled's movement to urge the plurality of staples from the cartridge for a predetermined time period when the anvil is in the closed position and in cooperative alignment with the staple cartridge. The surgical stapler also has an indicator connected to the controller. The controller controls the indicator to provide an indication when the predetermined time period is reached.

According to another embodiment of the present disclosure, there is provided a method for stapling tissue. The method includes the steps of locating tissue between a staple cartridge and an anvil and compressing tissue between the staple cartridge and the anvil. The method also has the step of manipulating an actuator to fire staples from the staples cartridge. The actuator is configured to automatically delay firing staples for a predetermined time period. The predetermined time period is suitable in length to allow compression of the tissue for the predetermined time period and to allow tissue to settle from a first initial state into a second compressed state. The method also has the steps of urging staples from the staple cartridge through the tissue at the elapse of the predetermined time period when the tissue is in the second compressed state.

According to another aspect of the present disclosure, the surgical stapler has a controller to place a delay between actuation of the firing mechanism component and actual firing of the staple.

According to another aspect of the present disclosure, the surgical stapler has a control device that controls a stroke parameter, a distance parameter and/or a time parameter of a firing mechanism component to increase a tissue compression time of the clamp.

According to still another aspect of the present disclosure, the surgical stapler has a motor and a first switch. The first switch is connected to a motor and delays the motor from actuating in order to achieve an amount of tissue compression by a clamp. The surgical stapler may have a second switch. The second switch senses another location of a drive screw and actuates a reverse function of the motor to return the drive screw to an initial position.

According to still yet another aspect of the present disclosure, the surgical stapler has an indicator that measure a distance traveled of the drive screw or a tissue compression time of the clamp.

According to still another aspect of the present disclosure, the surgical stapler has a visual indicator that indicates a position of the firing mechanism component or indicates a status condition of the surgical stapling.

In another embodiment of the present disclosure, there is provided a surgical stapler. The stapler has a handle assembly including a trigger and a clamping device with a staple cartridge including a plurality of staples and an anvil having a fastener forming surface thereon. The stapler has a controller configured to determine an occurrence of clamping by the anvil and the staple cartridge. The controller controls a firing of the plurality of staples from the staple cartridge. When the trigger is actuated the controller delays firing of the plurality of staples from the staple cartridge to provide for a predetermined time period of tissue compression of the tissue between the anvil and staple cartridge. The controller outputs a control signal to allow firing once the predetermined time period is reached.

DESCRIPTION OF THE DRAWINGS

Other and further objects, advantages and features of the present disclosure will be understood by reference to the following specification in conjunction with the accompanying drawings, in which like reference characters denote like elements of structure and.

DETAILED DESCRIPTION

Figure 1:
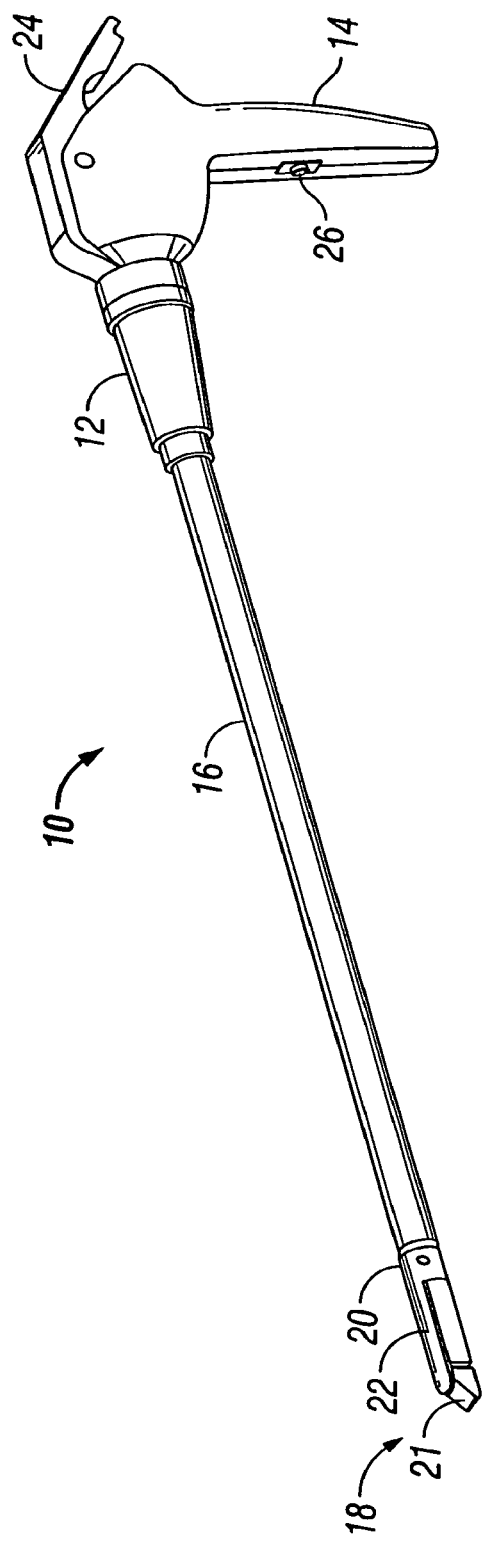
FIG. 1 is a perspective view of a first embodiment of a surgical stapler of the present disclosure.

In the drawings and in the description which follows, the term "proximal", as is traditional, will refer to the end of the apparatus which is closest to the operator, while the term "distal" will refer to the end of the apparatus which is furthest from the operator.

The present disclosure can be used with any stapler device known in the art and is intended to encompass the same, and is intended to be discussed in terms of both conventional and endoscopic procedures and apparatus. However, use herein of terms such as "endoscopic", "endoscopically", and "endoscopic portion", among others, should not be construed to limit the present disclosure to an apparatus for use only in conjunction with an endoscopic tube. The apparatus of present disclosure may find use in procedures in these and other uses including but not limited to uses where access is limited to a small incision such as arthroscopic and/or laparoscopic procedures, or other conventional medical procedures. The present mechanism may also be used with surgical stapling devices that have independent or combined clamping and firing procedures. The present disclosure may further be incorporated with surgical stapling devices that have simultaneous or dependent clamping and firing mechanisms. The present disclosure is also intended to be used with such surgical stapling devices which have a discrete clamping gradient.

Referring now to the figures, wherein like reference numerals identify similar structural elements of the subject disclosure, there is illustrated in FIG. 1 a self-contained, powered surgical stapler constructed in accordance with an embodiment of the subject disclosure and designated generally by reference numeral 10. The surgical stapler 10 is generally intended to be disposable, however the disposable arrangement is non-limiting and other non-disposable arrangements may be contemplated and are within the scope of the present disclosure.

The surgical stapler 10 of the present disclosure (shown in a perspective view in FIG. 1 and described herein) includes a frame generally represented by reference numeral 12 and handle generally represented by reference numeral 14. The frame 12 defines a series of internal chambers or spaces for supporting various inter-cooperating mechanical components of the surgical stapler 10 as well as a number of staples therein for the application to the body tissue.

The frame 12 supports a portion 16 or an extended tube-like portion. The portion 16 is capable of being rotated and has a relatively narrow diameter in a range of about 10 millimeters, and is for insertion into a small opening or tube inserted into the body, such as in the abdominal cavity, or other similar body cavities. The portion 16 has a longitudinal axis and has a length appropriate for reaching the operation site in the interior of the body. The surgical stapler 10 may be used in conjunction with other instruments such as endoscopes or other such optical devices for visually examining the interior of the body, for example, cameras by means of CCD devices, fiber optics or other optical or recording devices.

Generally, portion 16 of the surgical stapler 10 is inserted through the small opening or wound, and is manipulated to the operation site. The present disclosure is intended to be used with any surgical stapler including but not limited to surgical staplers having simultaneous clamping and independent clamping.

Portion 16 has a fastening assembly generally represented by reference number 18 and cutting assembly (not shown) that is known in the art. The fastening assembly 18 and the cutting assembly (not shown) are located in a housing 20 which carries a fastener and an optional cutter to the operation site. The fastening assembly 18 in this particular embodiment has a jaw or a staple cartridge 21 and a second jaw or anvil 22. The staple cartridge 21 and the anvil 22 may be brought into close cooperative alignment with one another so the jaws 21, 22 form a clamp therebetween. The jaws 21, 22 may be a first and second jaw that open and close or may be another different clamping type structure as is known in the art. The staple cartridge 21 may be located at the distal end of the housing 20, in the jaws 21, 22 themselves or may be located in other locations as described in U.S. Pat. No. 7,044,353 to Mastri, et al. which is herein incorporated by reference in its entirety. The staple cartridge 21 has one or a number of rows of staples. The surgical stapler 10 also has an anvil (not shown) and further may include an optional knife (not shown) as is well known in the art for accomplishing the stapling. It is appreciated that the closing of the jaws 21, 22 with the staple cartridge 21 and the anvil 22 may be accomplished by pivoting the anvil 22 relative to the staple cartridge 21, or by pivoting the staple cartridge 21 relative to the anvil 22, or by pivoting both the staple cartridge 21 and the anvil 22 relative to one another.

Generally, actuating the operating portion of the fastening assembly 18 is accomplished via intermediate components disposed on or within the narrow longitudinally extending tubular portion 16. In one non-limiting embodiment, a cylindrical tubular sleeve member surrounds the portion 16. The sleeve may be manipulated in a direction with the longitudinal axis of the surgical stapling device. The sleeve slides onto the anvil 22 for closing the jaws 21, 22 that are biased open by a biasing device (not shown) to accomplish the clamping. The surgical stapler 10 of the present disclosure has three basic actions or functions, however, the present disclosure is intended to be used with any surgical stapler including but not limited to surgical staplers having simultaneous clamping (i.e., clamping and firing the stapler at the same time) and independent clamping (i.e., clamping prior to the staple firing).

First, portion 16 is introduced into the human or animal body and is positioned with the jaws 21, 22 aligned at the desired stapling site to receive the target tissue. This may involve rotation of the portion 16 relative to the body, either by rotating the surgical stapler 10 as a whole, by rotating simply the portion 16 relative to the frame 12 as permitted, or a combination of both actions. Thereafter (i.e., secondly), the surgical stapler 10 secures the target body tissue between the staple cartridge or jaw 21 in the distal portion of the housing 20 and the anvil 22. This is accomplished by a clamping action of the jaws 21, 22 or alternatively by another similar or different clamping member.

The jaws 21, 22 are allowed to remain in the closed position for a desired period of time depending on the particular tissue. By configuring the jaws 21, 22 to remain closed for a predetermined period of time allows any excess liquid or fluid in the tissues to drain out of the body tissues prior to actuation of the stapling cartridge 21. This ensures that the liquid does not traverse out of the tissues after firing to form non-uniform staples and instead ensures a proper and uniform staple formation.

With the target tissue clamped between the anvil 22 and the staple cartridge 21, a camming surface which surrounds the housing 20 and anvil 22 is employed to close the jaws 21, 22 of the surgical stapler 10 and clamp the tissue between the anvil 22 and the tissue contacting surface of the staple cartridge 21. The jaws 21, 22 are clamped by actuation of a lever 24 opposite the jaws 21, 22 as is known in the art. Thereafter, the surgeon applies the staples to the body tissue. A longitudinally extending channel is employed to deliver longitudinal motion to an axial drive member and a tissue cutting knife as is known in the art.

The axial drive member or an axial drive screw contacts pusher elements. The pusher elements drive the staples through the body tissue against the fastener or forming surface of the anvil as discussed herein. Typically, in the art the surgical stapler 10 fires usually by an actuation of a first trigger handle or alternatively using a trigger switch 26. Thereafter, the clamping action of the jaws 21, 22 is released and the surgical stapler 10 or a portion thereof may be withdrawn from the body.

Figure 2:
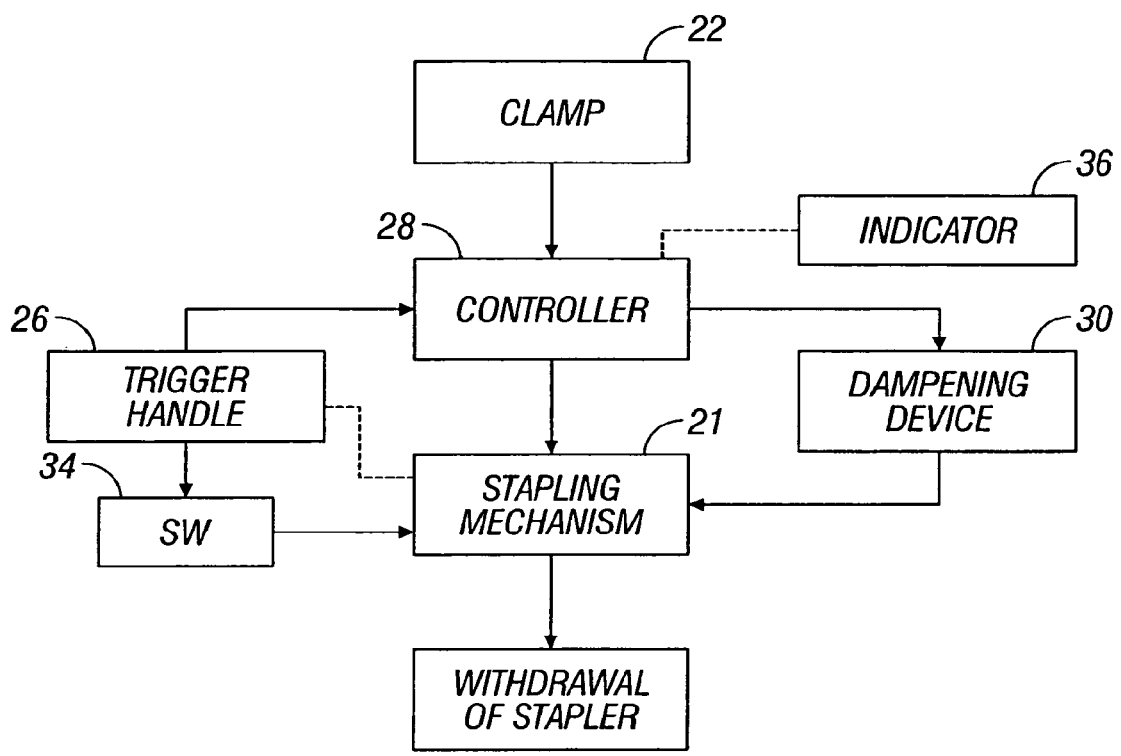
FIG. 2 is a block diagram of a number of components of the surgical stapler of FIG. 1.

Referring now to FIG. 2, there is shown a block diagram of the surgical stapler 10 of the present disclosure. According to a first aspect of the present disclosure, the surgical stapler 10 may have an optional controller 28. The controller 28 is any electronic device being coupled to a memory for executing one or more readable program instructions or alternatively may be a suitable analog circuit. Still further, the controller 28 may be a suitable mechanical member or linkage for controlling one or more functions of the surgical stapler 10.

The controller 28 is connected to an internal or external power supply and a motor and is connected between the anvil 22 and the stapling cartridge 21. In an alternative embodiment, a trigger handle or another actuating switch or component 26 is mechanically or electronically linked or otherwise connected to the stapling cartridge 21 as is known in the art as indicated by a dotted line, and the present disclosure is not intended to be limited to any configuration. Once the stapling cartridge 21 is fired using the trigger switch 26, the jaws 21, 22 are opened and the firing mechanism is retracted. The surgical stapler 10 as a whole may be withdrawn from the body tissue or may be manipulated for a next or second stapling operation as shown.

The present surgical stapler 10 has the controller 28 which is connected to one of the jaw or anvil 21 or jaw or staple cartridge 21 and the trigger switch 26 or is connected to both jaws 21, 22 and the trigger switch 26. In one embodiment, once the desired site is reached, the surgeon uses the jaws 21, 22 to compress the selected body tissue. Alternatively, the surgical stapler 10 may have a single drive component that can actuate both the anvil 22 and stapling cartridge 21.

Thereafter, the controller 28 may provide for a requisite amount of delay between clamping and firing (or after clamping and before firing) to ensure tissue compression and expulsion of fluid. After the desired compression is reached, the stapling cartridge 21 may be automatically engaged by the controller 28 to fire the staples from the stapling cartridge 21 into the body tissue or alternatively the controller 28 may send a signal to the surgeon thereby informing the surgeon a suggestion that the surgeon is to fire the staples. It is envisioned that the firing may be automatic or manual.

Furthermore, the controller 28 may control the speed with which the staples are fired from the staple cartridge 21. Still further, the controller 28 may control an amount of delay before firing. The controller 28 in one embodiment may provide for a predetermined amount of time to elapse prior to outputting a signal to the stapling cartridge 21. In another powered stapler embodiment, the controller 28 may slow a motor speed to increase the body tissue compression time.

In still another embodiment, the controller 28 may engage a dampening device 30. The dampening device 30 is configured to slow the actuating of the staple cartridge 21 in order to increase the overall compression time of the body tissue. Such a dampening device 30 may be a hydraulic or a pneumatic type damper or any other device that may dampen or modulate the operation of one or more components of the surgical stapler 10. In another embodiment, the trigger 26 may simply hold the fire signal for a predetermined time period in associated control circuitry and upon the expiration of the predetermined time period may communicate the signal to the stapling cartridge 21.

The controller 28 may be configured to slow a motor speed, modulate a gear or, still further, engage a circuitry of the motor to slow an operation thereof to otherwise reduce actuation, i.e., a rotation rate of the axial drive screw. Still further, the surgical stapler 10 may also include an override switch 32. The override switch 32 is an automatic or manual device (or other switch) that selectively disengages the controller 28 to permit direct actuation of the stapling cartridge 21 by the trigger switch 26 without any delay at the surgeon's discretion.

Figure 2A:
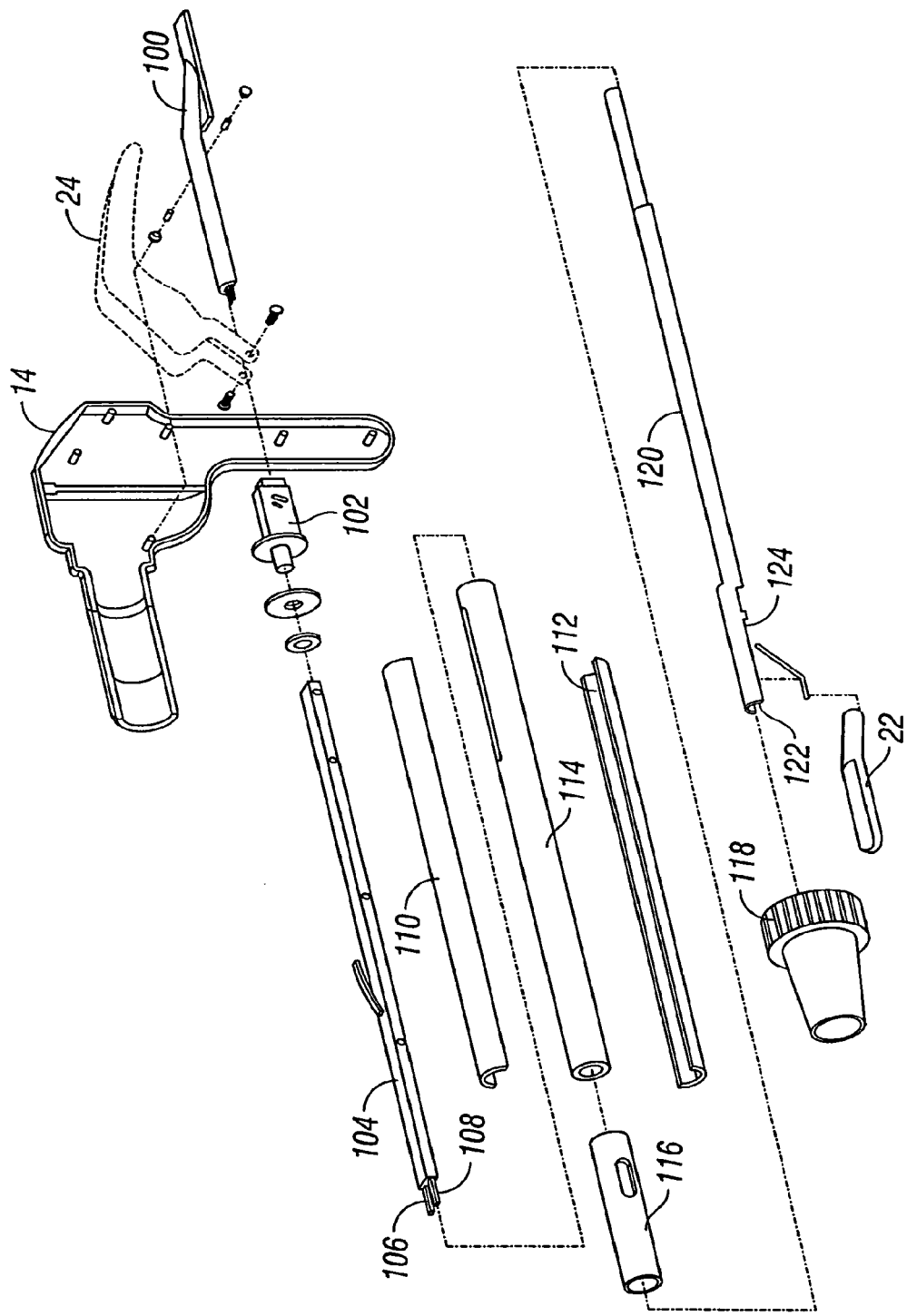
FIG. 2A is an exploded view of a channel of the surgical stapler of FIG. 1.
Figure 2B:
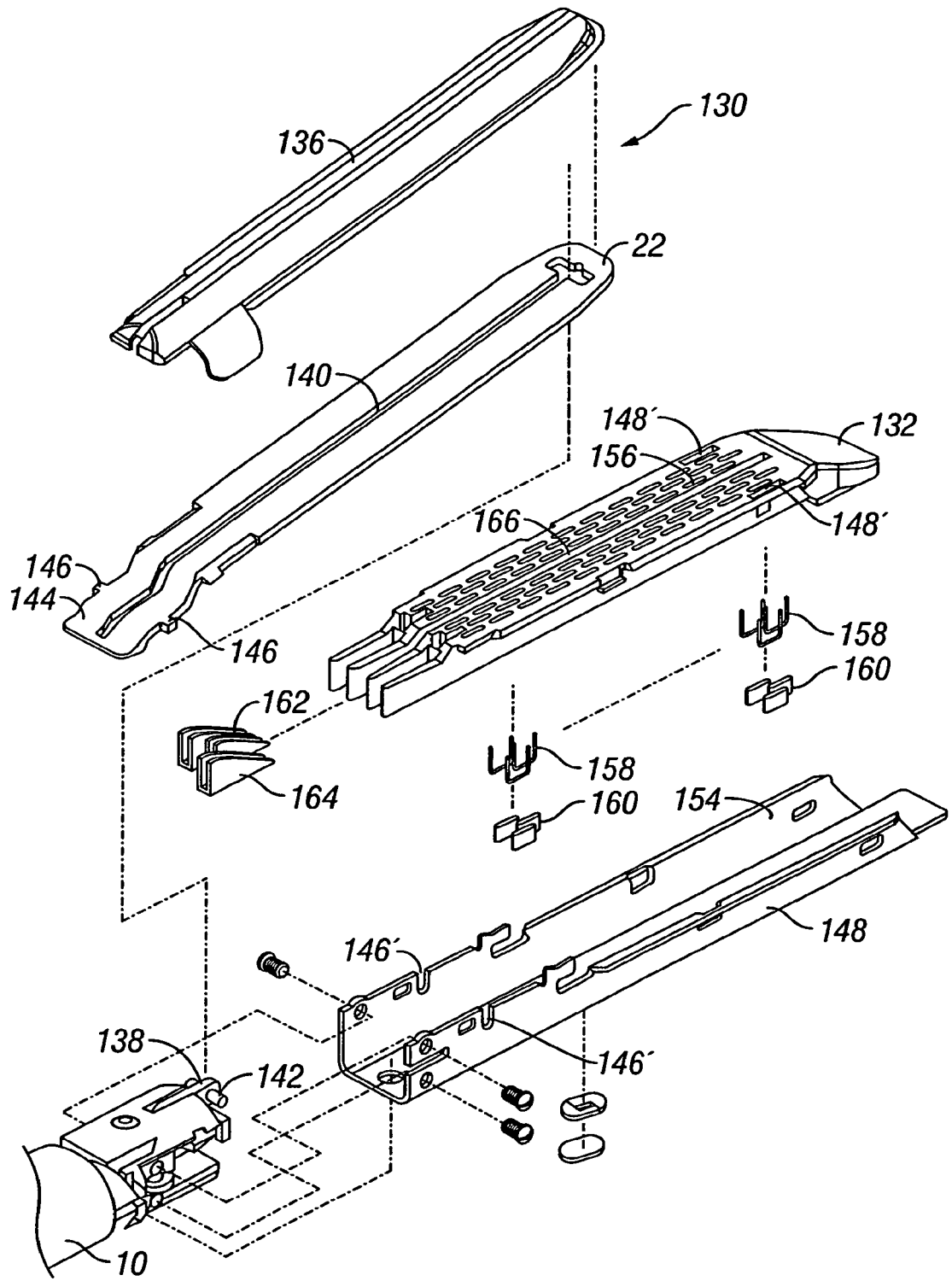
FIG. 2B is an exploded view of the staple cartridge, anvil and the drive sled of FIG. 1.

In one aspect of the present disclosure, the present surgical stapler 10 includes jaws 21, 22 which compresses tissue between the anvil 130 and the stapler cartridge 132 of the stapling cartridge 21 (FIG. 2B). The jaws 21, 22 are understood in the art as a device that allows the surgeon to manipulate and compress tissue between the anvil 130 and the staple cartridge 132 prior to urging of the staples 158 from the staple cartridge 132 as shown in FIG. 2B. The jaws 21, 22 may be independently powered by a power source such as a motor or pneumatic device, or may be powered by the same power source as the staple cartridge 21. The surgical stapler 10 uses the jaws 21, 22 to clamp tissue between the stapler cartridge 132 and the anvil 130 (FIG. 2b), then when the stapler 10 is fired the jaws 21, 22 may be further tightened and then the staples 158 urged from the stapling cartridge 21.

In one aspect, the surgical stapler 10 may pre-clamp or compress tissue using the jaws 21, 22 for a first interval. The first time interval may be preset and fixed, or variable depending on the tissue type. The first time interval may be for minutes, seconds or any other variable or fixed predetermined period of time. Then prior to stapling, the jaws 21, 22 may further tighten to further compress the tissue for another second compression time interval and then fire. The second time interval may be different from the first time interval and can be shorter or longer than the first. In another aspect, the instrument may pre-clamp or compress tissue using the jaws 21, 22 and then simply automatically fire the device to urge the staples 158 from the staple cartridge 132 at the conclusion of the first interval. Various configurations are possible, and the present surgical stapler 10 may have program instructions for any number of compression intervals desired by the surgeon and/or designer. The surgical stapler 10 may alternatively further use a second separate clamping device in association with the stapler 10. It is understood that the present disclosure may be incorporated into an instrument that approximates the tissue before firing such as with a TA surgical stapler such as U.S. Pat. No. 6,817,508 to Racenet, et al. which is herein incorporated by reference in its entirety, or can be used with an instrument that requires no such approximation before firing.

In another embodiment of the present disclosure, the surgical stapling device 10 may provide the surgeon with feedback by virtue of an indicator 36. The indicator 36 may display an amount of compression, time and/or provide feedback of the status of the stapling, or display information relating to the location of the drive screw, or drive member. In another embodiment of the present disclosure, the surgical stapler 10 may not have separate clamping and firing actuators and include a clamping gradient indicator 36 or simultaneous clamping and firing indication mechanism. For example, the surgical stapler 10 may be configured to allow control of the firing speed which, in turn, controls the clamping speed and timing and then provide optimal compression for squeezing the tissue and pushing the blood and fluid out of the tissue at the desired site.

FIG. 2A shows an exploded view of a number of components of the surgical stapler 10 of FIG. 1. The stapler 10 has a rack 100 that is slidable in the handle portion 14. The rack 100 interfaces with a clamp tube 102. On a distal side of the clamp tube 102 is a channel 104. The channel 104 engages with the clamp tube 102 and a pair of forks 106, 108 on a distal side thereof. The stapler 10 also has an upper cover 110 and a lower cover 112, and an extension tube 114. The extension tube 114 engages with a collar tube 116. The stapler 10 also has a rotation knob 118 with a channel portion 120. The channel portion 120 has a pair of camming surfaces 122 on a distal end. The distal end also has a crimp 124 in a distal side to receive the anvil 22.

In operation, the rack 100 slides and moves the clamp tube 102 distally. The clamp tube 102 is provided to interconnect the handle portion 14 and the extension tube 114. The channel 104 is slidably mounted for reciprocal longitudinal motion. The extension tube 114 provides support for the surgical stapler 10 and has slots that interface with the collar tube 116. The surgical stapler 10 also has a support 120 for longitudinal motion and to operate the stapling mechanism as described in FIG. 2b. The operation of these components is well known and is disclosed in U.S. Pat. No. 5,318,221 to Green, et al., which is herein incorporated by reference in its entirety.

Advantageously, the rack 100 moves distally to advance the channel 104 in a distal manner. The channel 104 delivers longitudinal motion to a pusher cam bar as is known in the art for operation of the stapler cartridge 21 shown in FIG. 2b. It should be appreciated that the components shown in FIG. 2a only illustrate one embodiment of the present surgical stapler 10, and instead of the rack 100, the surgical stapler 10 may have a drive screw (not shown) for longitudinal motion and in order to actuate the stapler cartridge 21. Referring now to FIG. 2b, there is shown an exploded view of the anvil 22 and the stapler cartridge 132 having an actuation sled 169.

Referring to FIG. 2b, the stapler cartridge 21 includes an anvil assembly 130 and a cartridge assembly 132 shown in an exploded view for illustration purposes. The anvil assembly 130 includes anvil portion 22 having a plurality of staple deforming concavities (not shown) and a cover plate 136 secured to a top surface of anvil portion 134 to define a cavity (not shown). The cover plate 136 prevents pinching of tissue during clamping and firing of the surgical stapler 10. The cavity is dimensioned to receive a distal end of an axial drive assembly 138.

The anvil 130 has a longitudinal slot 140 that extends through anvil portion 130 to facilitate passage of retention flange 142 of the axial drive assembly 138 into the anvil slot 140. A camming surface 144 formed on anvil 22 is positioned to engage axial drive assembly 138 to facilitate clamping of tissue. A pair of pivot members 146 formed on anvil portion 130 is positioned within slots 146' formed in carrier 148 to guide the anvil portion 130 between the open and clamped positions.

The stapler 10 has a pair of stabilizing members 152 engage a respective shoulder formed on carrier 148 to prevent anvil portion 30 from sliding axially relative to staple cartridge 132 as camming surface of the anvil 130 is deformed. Cartridge assembly 132 includes the carrier 148 which defines an elongated support channel 154. Elongated support channel 154 is dimensioned and configured to receive the staple cartridge 132 which is shown above the carrier 148 in the exploded view of FIG. 2b. Corresponding tabs and slots formed along staple cartridge 132 and elongated support channel 148' function to retain staple cartridge 132 within support channel 154 of carrier 148. A pair of support struts formed on the staple cartridge 132 are positioned to rest on side walls of carrier 148 to further stabilize staple cartridge 132 within support channel 154, however other arrangements to support the cartridge 132 on the channel 154 can be used and this arrangement is not limiting.

Staple cartridge 132 includes retention slots 156 for receiving a plurality of fasteners 158 and pushers 160. Longitudinal slots 156 extend through staple cartridge 132 to accommodate upstanding cam wedges 162 of the actuation sled 164. A central longitudinal slot 166 extends along the length of staple cartridge 132 to facilitate passage of a knife blade (not shown). During operation of surgical stapler 10, actuation sled 164 is drive distally to translate through longitudinal slot 156 of staple cartridge 132 and to advance cam wedges 162 distally and into sequential contact with pushers 160, to cause pushers 160 to translate vertically within slots 156 and urge fasteners 158 from slots 156 into the staple deforming cavities of anvil assembly 130 to effect the stapling of tissue.

Figure 3:
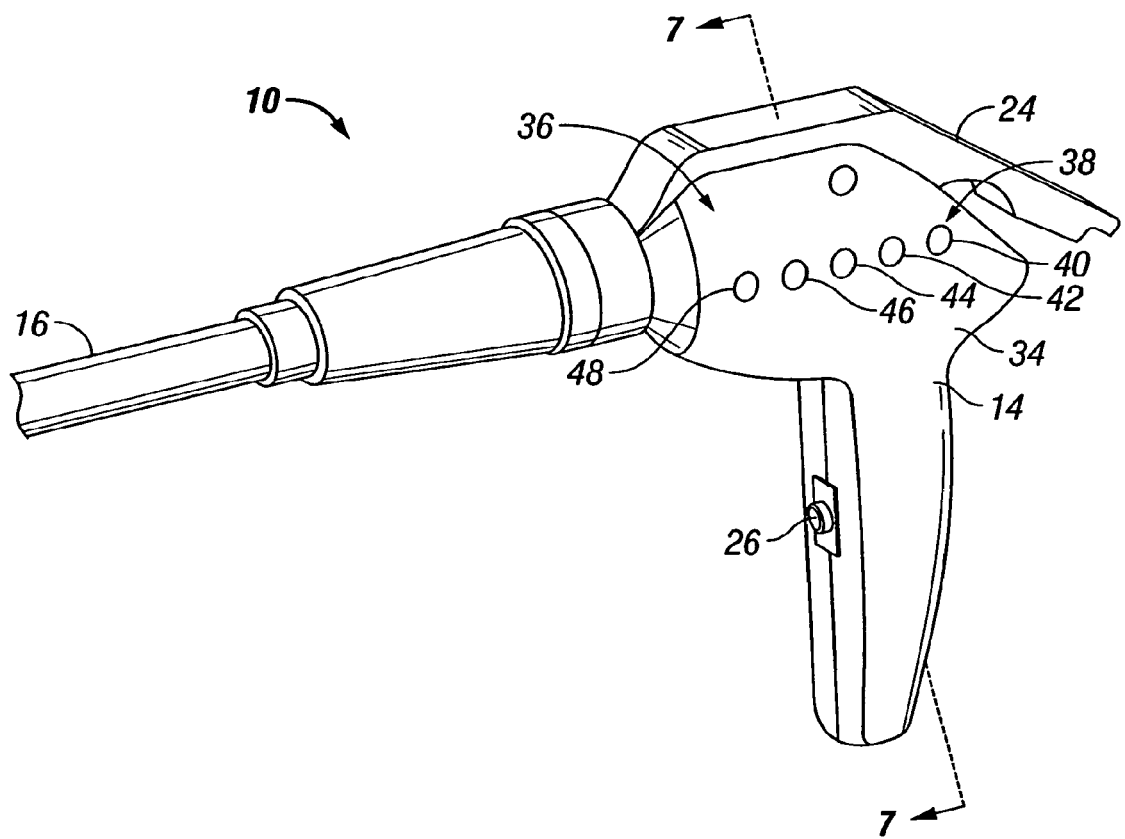
FIG. 3 is a perspective view of another embodiment of the surgical stapler of the present disclosure having a plurality of lights.

Referring to FIG. 3, the surgical stapler 10 may include indicator 36 which may be any device known in the art to provide sensory feedback to the surgeon. The indicator 36 may be any device that permits a visual, tactile or audible monitoring of one or more conditions of the surgical stapler 10. The indicator 36 may be disposed on outer surface 34 and disposed on the handle 14. Alternatively, the indicator 36 may be disposed on portion 16, on the trigger switch 26, on the lever 24 or in any other suitable location where the indicator 36 may be easily viewed by the surgeon without a change in position of change in footing by the surgeon.

In one embodiment, as shown the indicator 36 includes a number of light bulbs 38. The lights 38 may be one light or a series of many lights bulbs or LEDs with one color or an assortment of two or more colors. Each of the lights 38 may have a color representing one or more conditions of the surgical stapler 10. Alternatively, one or all of the lights 36 may flash to indicate a condition of the surgical stapler 10.

Upon being actuated by the trigger switch 26, the surgical stapler 10 may impart a delay before firing of the staples. However, in order to provide the proper feedback to the surgeon, the lights 38 provide, for example, a visual indication of the progress of the firing of the stapling cartridge 21. For example, still referring to FIG. 3, there is shown a first light 40, a second light 42, a third light 44, a fourth light 46, and a fifth light 48. As the axial drive screw (not shown and in the handle) travels the predetermined drive path the lights 40, 42, 44, 46, and 48 illuminate in series to portray the relative distance of the drive screw on the exterior of the handle. When the lights 40, 42, 44, 46, and 48 are illuminated, the stapling cartridge 21 fires which ensures that proper tissue compression occurs prior to deployment of the staples.

Figure 4:
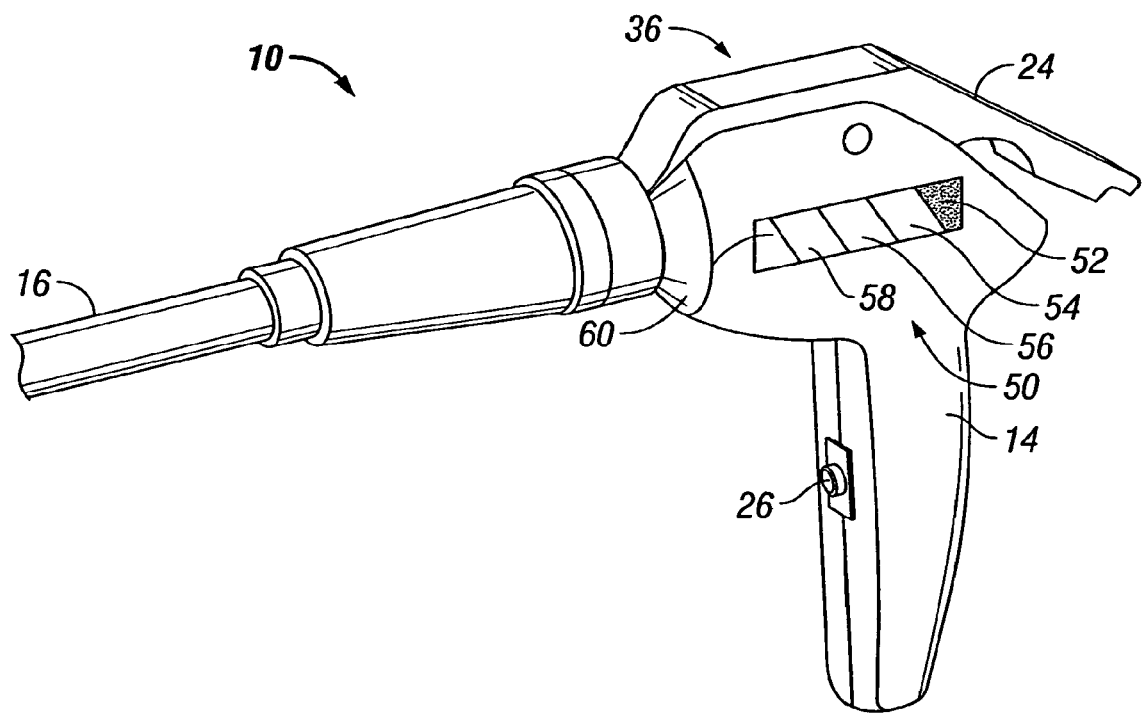
FIG. 4 is a perspective view of still another embodiment of the surgical stapler with a linear indicator or display.

Referring now to FIG. 4, in another exemplary embodiment of the present disclosure, the surgical stapler 10 includes a linear indicator 50 having a plurality of discrete segments, first segment 52, second segment 54, third segment 56, fourth segment 58, and fifth segment 60. Again, once the trigger switch 26 is actuated to fire the stapling cartridge 21, the segments 52, 54, 56, 58, and 60 each illuminate in a predetermined pattern to indicate to the surgeon the status of the progression of the drive screw in the handle 14.

Upon all of the segments 52, 54, 56, 58, and 60 being illuminated, the stapling cartridge 21 fires the staple into the body tissue with assurance that an amount of compression time of the body tissue has lapsed. Linear display 50 may have one or more different colors or combinations of colors to indicate a position of the drive screw such as "red" to indicate firing and "green" to indicate that the firing is complete or vice versa. Still further the linear display 50 may display one or more graphical representations, images, or pictures to indicate one or more conditions or operating parameters of the surgical stapler 10.

For example, the linear display 50 may indicate "FIRE" or "COMPLETE", or any other graphical representation to indicate that surgical stapler 10 will fire at the predetermined time period. Various possible combinations are possible and all are within the scope of the present disclosure.

Figure 5:
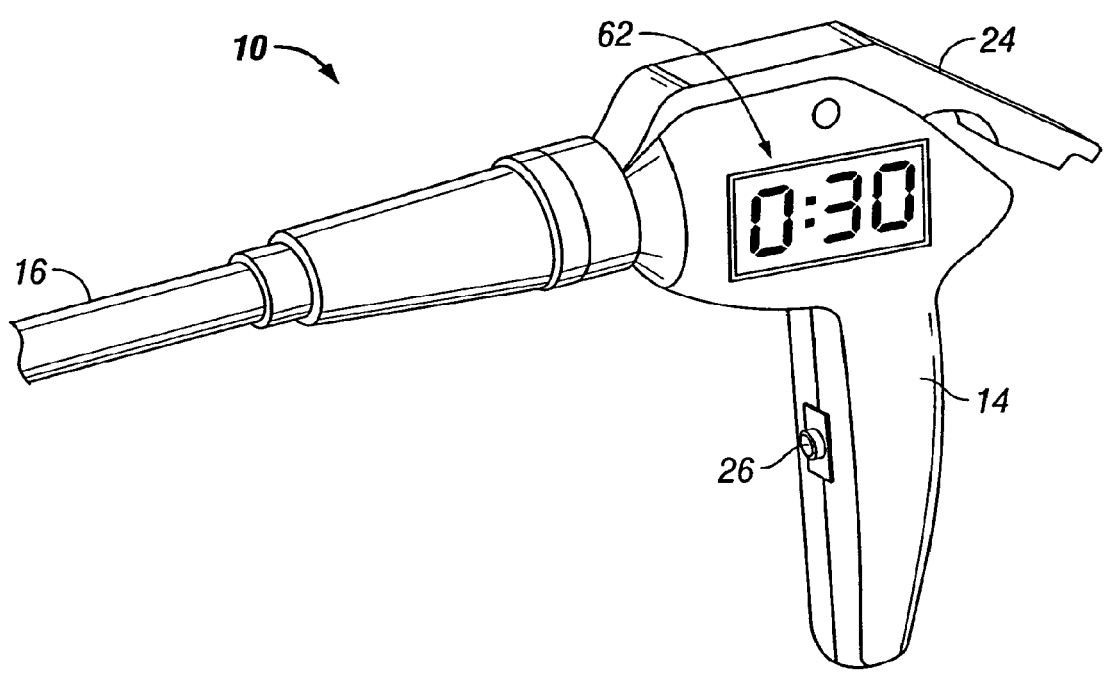
FIG. 5 is a perspective view of yet another embodiment of the surgical stapler having a digital indicator or display.

In still another exemplary embodiment of the present disclosure shown in FIG. 5, the surgical stapler 10 may include a digital display 62. The digital display 62 may indicate a count down or count up (or other time interval) after actuation of the trigger switch 26. For example, the digital display 62 may count down to the desired stapling time after compression to ensure a predetermined amount of tissue compression by the jaws 21, 22. The digital display 62 may be activated by the jaws 21, 22 being brought in close alignment with one another or activated independent of clamping. A desired clamping interval may be preset for desired tissue.

Alternatively, the digital display 62 may be selectively preset and input by the surgeon using an input device (not shown) or button. The surgeon may input a time period of clamping into the display 62. Thereafter, the display 62 will suggest firing at the elapse of the clamping time period, or may automatically fire after a predetermined clamping time elapses (e.g., such as from about ten seconds to forty five seconds) to ensure proper tissue compression. The digital display 62 may be configured to count down from the predetermined set interval of clamping and visually communicate a signal to the controller 28. The controller 28 after receiving the signal allows the desired time period of clamping to elapse. After the set time period expires, the controller 28 may communicate a second signal to actuate the stapling cartridge 21. Alternatively, the controller 28 may simply modulate the speed of the motor to commence operation at a speed suitable to actuate the stapling cartridge 21 at the end of the desired time period. In still yet another embodiment, the digital display 62 may be configured to initiate counting after commencement of the clamping of tissue and then simply display the time from that point onwards to allow the surgeon to monitor and manually actuate the trigger switch 26 at the expiration of the desired time period. Thereafter, the digital display 62 may simply display or flash the compression time to the surgeon and the exact amount of elapsed time. It is appreciated that the instrument may provide a predetermined delay and then indicate that the instrument is ready to be manually fired, or alternatively the instrument may delay then indicate and then automatically fire.

Figure 6:
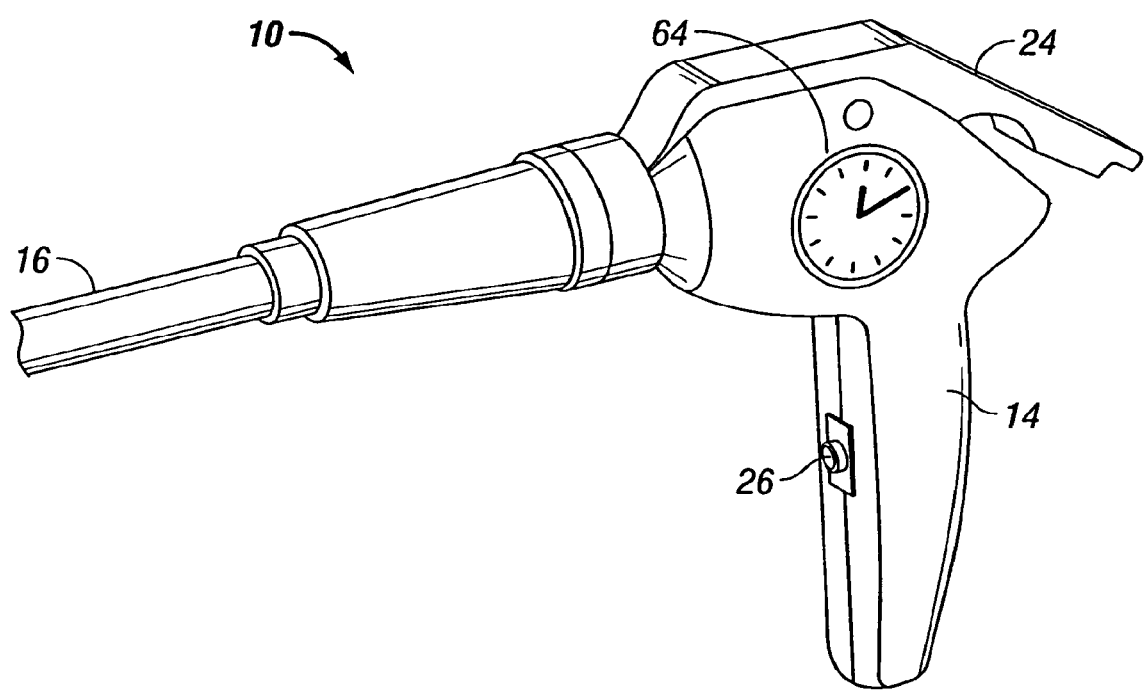
FIG. 6 is a perspective view of still another embodiment of the surgical stapler with an analog indicator or display.

Referring now to FIG. 6, the surgical stapler 10 may alternatively have an analog display 64 disposed on the outer surface of the handle 14 which functions similar to the digital display 62. Analog display 64 may have an audible alarm or alternatively have a flashing light to indicate that the appropriate tissue compression time has been reached or exceeded.

Figure 7:
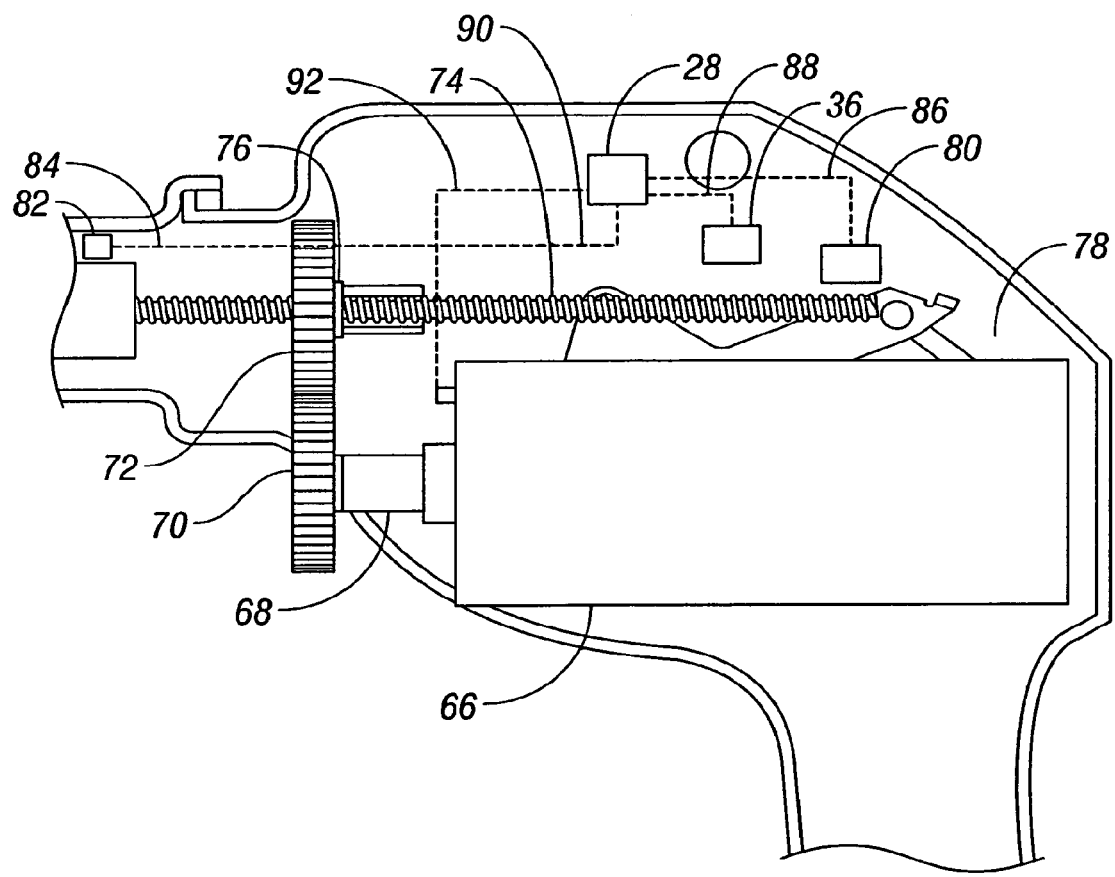
FIG. 7 is a cross sectional view of the surgical stapler of FIG. 3 along line 7-7.

Referring now to FIG. 7, there is shown a cross sectional view of the handle 12 of the surgical stapler along line 7-7 of FIG. 3. In this embodiment, the surgical stapler 10 is a powered device and has a motor 66 with a driving mechanism. The driving mechanism is a drive output shaft 68. Shaft 68 connects to a first gear 70. The first gear 70 is connected to a second gear 72 which, in turn, engages an axial drive screw 74. The motor 66 may be a device that drives one or more components of the surgical stapler 10.

The drive screw 74 is a threaded rod having a number of helical grooves that are intended to rotate and contact another member to actuate the stapling cartridge 21 in the distal location of the surgical stapler 10 once compression is made by the surgeon using the clamp or jaws 21, 22. The axial drive screw 74 is disposed in toothed engagement through a central bore 76 of the second gear 72. The axial drive screw may also be disposed offset from the second gear 72 or in any other desired geared arrangement. Upon actuation of the motor 66, the axial drive screw 74 rotates and traverses distally through the portion 16 of the surgical stapler 10 to engage the stapler cartridge 21 as is well known in the art. Alternatively, the surgical stapler 10 may have a drive piston or plunger instead of the axial drive screw 74 or a single drive mechanism to control both the anvil 22 and the stapling cartridge 21. Such mechanisms are well known in the art and may be found in U.S. Pat. No. 6,330,965 B1 to Milliman, et al., U.S. Pat. No. 6,250,532 B1 to Green, et al., U.S. Pat. No. 6,241,139 B1 to Milliman, et al., U.S. Pat. No. 6,109,500 to Alli et al., U.S. Pat. No. 6,202,914 B1 to Geiste, et al., U.S. Pat. No. 6,032,849 to Mastri, et al. and U.S. Pat. No. 5,954,259 to Viola, et al., which are all herein incorporated by reference in their entirety.

The surgical stapler 10 may include a first switch 80. Switch 80 is located in a fixed position of the handle as shown. The stapler 10 also has a second switch 82 disposed distally relative to the first switch 80 that is distal or near the path of the drive screw 74 in the first initial position 78. Likewise, the second switch 82 in a second firing position 84 which is disposed distally from the first initial position and proximal or near the path of the drive screw 74. Each of the first and second switches 80, 82 is a limit switch, but alternatively may be any switch known in the art to change or toggle from a first position to a second position by a simple motion of the axial drive screw 74 traversing past or adjacent to the respective limit switch.

Once the axial drive screw 74 or a portion thereof traverses past the first switch 80, the first switch communicates a signal to the controller 28 by lead 86. The controller 28 thus illuminates the indicator 36 or a portion thereof by lead 88 to indicate to the surgeon a first location of the axial drive screw 74.

Thereafter, the drive screw 74 or a portion thereof traverses or contacts the second switch 82 at the second firing position 84. The second switch 82 is also a limit switch and communicates a second signal to the controller 28 by lead 90 of the location or firing of the stapler cartridge 21. The controller 28 then illuminates indicator 36 (or another portion thereof) by lead 88 to indicate to the surgeon that the stapling has been completed. At the conclusion of the stapling, the surgeon/operator will initiate retraction and then will reverse a direction of the motor 66 by lead 92. The motor 66 then reverses operation and returns the axial drive screw 74 to the initial position 78 for the next stapling operation.

Alternatively, controller 28 upon receiving the first signal from the first switch 80 by lead 86 modulates one or more operations of the surgical stapler 10. For example, in response to receiving of the first signal, the controller 28 can control one or more parameters of the surgical stapler 10 including tissue gap, speed of the motor 66, control stroke of the axial drive screw 74, axial drive screw travel distance, rotational rate of the axial drive screw and any combinations thereof.

Figure 8:
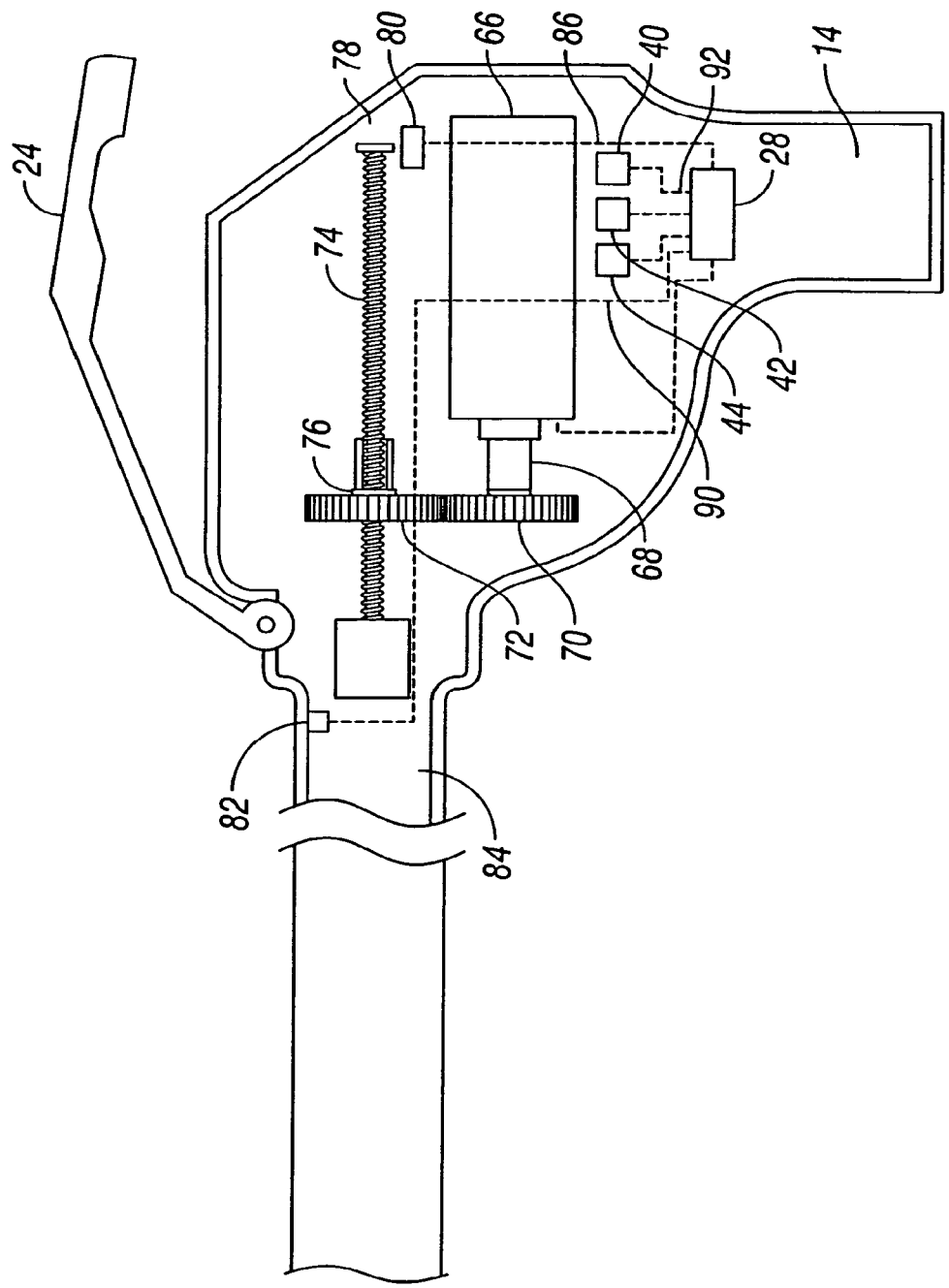
FIG. 8 is another cross sectional view of still another embodiment of the surgical stapler of the present disclosure along line 7-7 of FIG. 3 with the stapler having a first switch and a second switch.

Referring now to FIG. 8, the surgeon may operate/engage the firing mechanism in order to actuate the stapling cartridge 21. The firing mechanism actuates the motor 66 shown in FIG. 8. The axial drive screw 74 commences rotation and by traversing past switch 80 the drive screw 74 actuates the first switch 80. The first switch 80 outputs the signal to the controller 28 by lead 86. The controller 28 in response to the signal from the first switch 80 then actuates the first light 40 by lead 92. The surgical stapler 10 may further have a suitable structure in order to engage a stop feature. The stop feature prohibits overdrive of the drive screw 74.

Thereafter, after the axial drive screw 74 traverses a predetermined distance to ensure tissue compression by the clamp or jaws 21, 22. The second switch 82 is actuated and outputs a second signal to the controller 28 by lead 90. The controller 28 in response to the second signal illuminates the second light 42 by lead 94. The second light 42 indicates that the stapling cartridge 21 has fired. The second switch 82 may further emit a signal to the controller 28 to reverse or cease motion in that direction of the motor 66 or to return the axial drive screw 74 to the initial position. The physician/operator may also manually reverse the direction of the motor 66. A third light 44 may illuminate to indicate to the surgeon that the axial drive screw 74 is returning to the initial position 78.

Figure 8A:
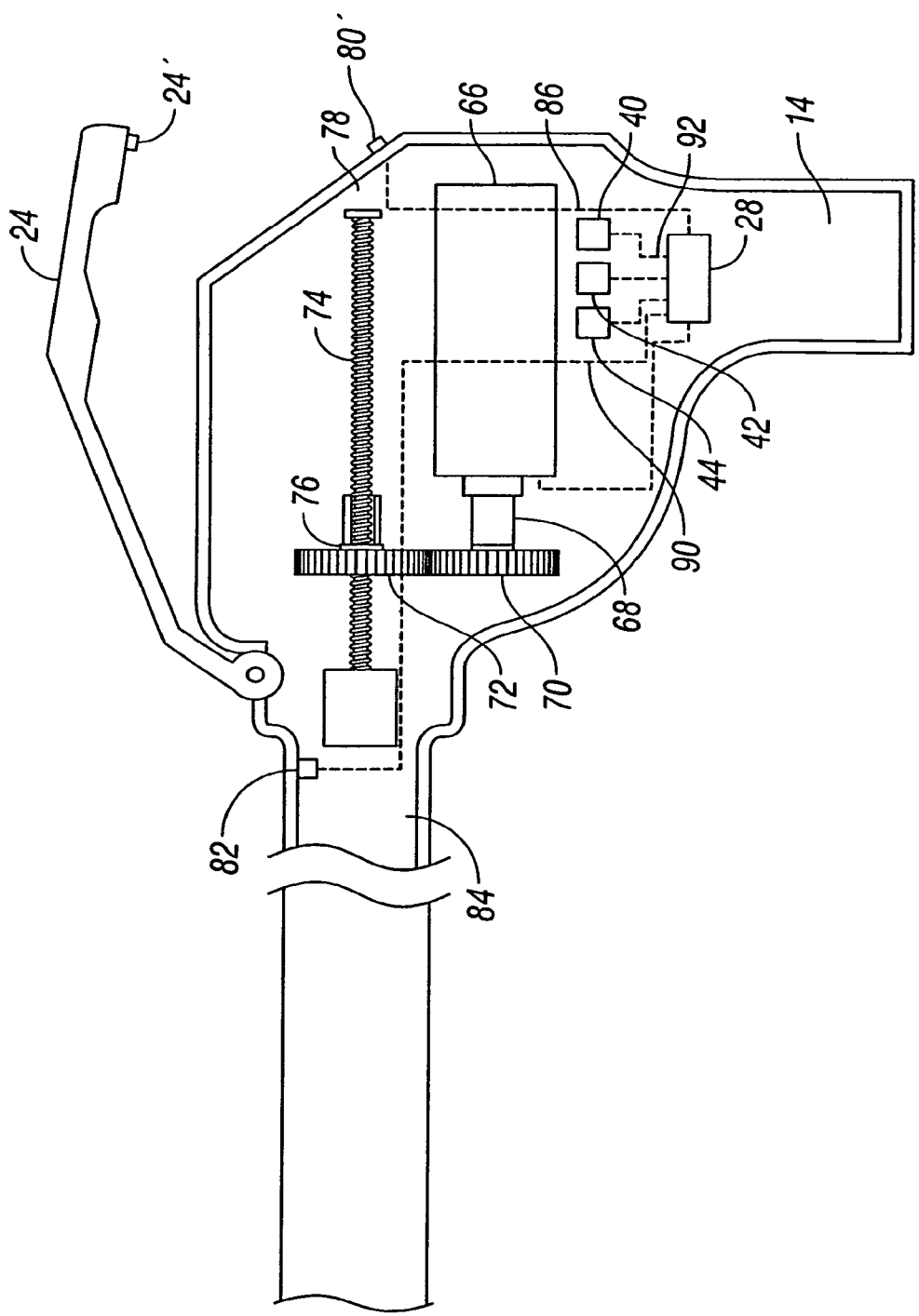
FIG. 8A is another cross sectional view of another embodiment of the stapler of FIG. 8 having the first switch which engages a tab on the lever.

FIG. 8A illustrates another embodiment of the present stapler. In the embodiment shown, the surgeon may operate/engage the firing mechanism in order to actuate the stapling cartridge 21. However, the first switch 80' is in a different location than the embodiment shown in FIG. 8. In this embodiment, the first switch 80' is located immediately under the lever 24 proximal to handle 14. The switch 80' in the embodiment of FIG. 8A engages a tab 24' disposed on the lever 24. When the lever 24 is actuated and driven toward the handle 14, the tab 24' contacts switch 80', and the switch 80' outputs the signal to the controller 28 by lead 86. The controller 28 in response to the signal from the first switch 80 then actuates the first light 40 by lead 92.

Thereafter, after the axial drive screw 74 traverses a predetermined distance to ensure tissue compression by the clamp or jaws 21, 22, the second switch 82 is actuated and outputs a second signal to the controller 28 by lead 90. Again, the controller 28 in response to the second signal illuminates the second light 42 by lead 94. The second light 42 indicates that the stapling cartridge 21 has fired. The second switch 82 that is actuated by switch 80' may further emit a signal to the controller 28 to reverse or cease motion in that direction of the motor 66 or to return the axial drive screw 74 to the initial position. A third indicator 44 may be included to indicate to the surgeon that the axial drive screw 74 is returning to the initial position 78.

Figure 8B:
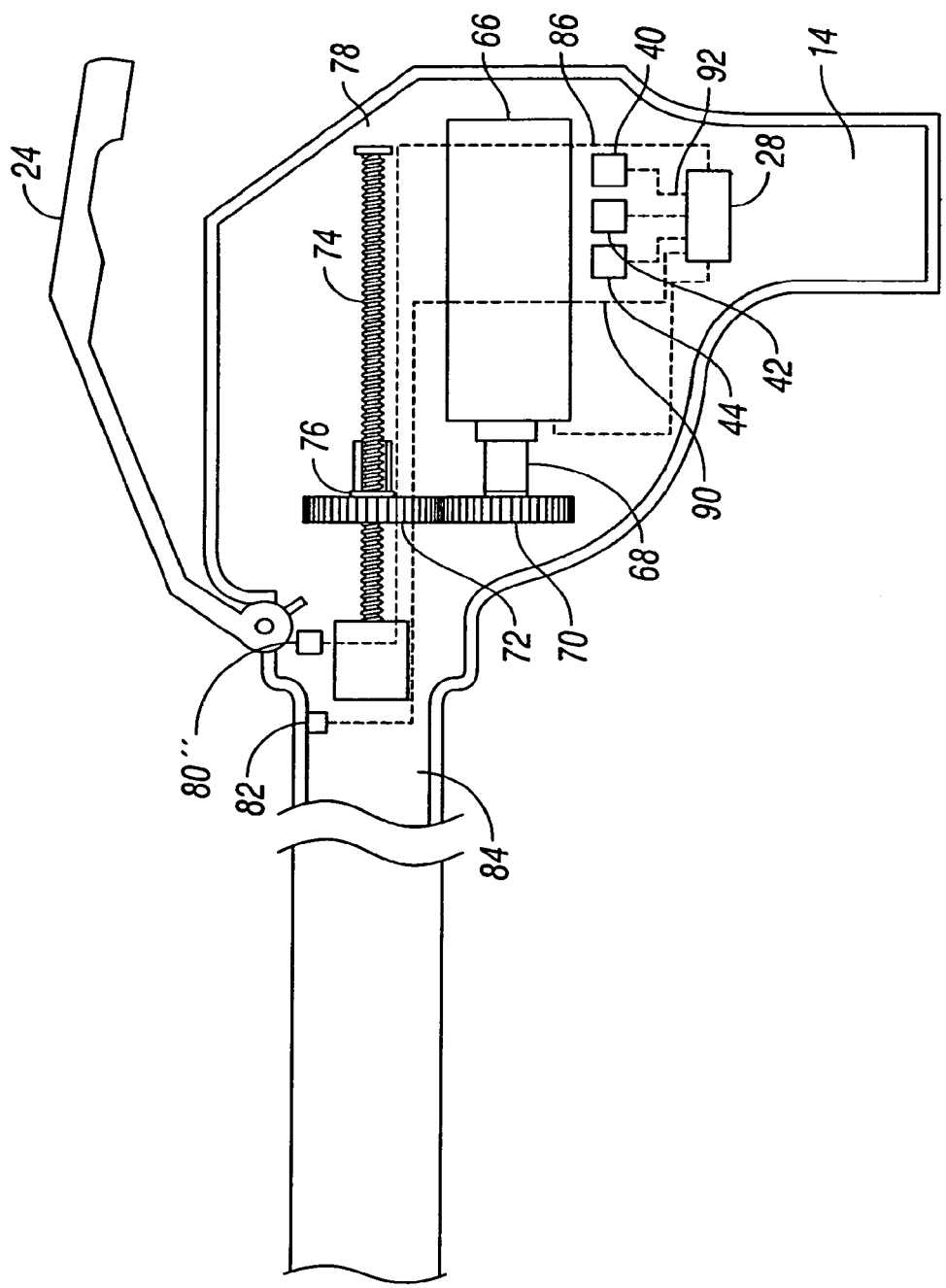
FIG. 8B is still another cross sectional view of yet another embodiment of the stapler of FIG. 8 having the first switch located distally on the lever.

FIG. 8B shows still another embodiment wherein the first switch 80" is located at still another location of the handle 14, and on an opposite distal side of the lever 24 in proximity to pivot. Various configurations are possible and within the scope of the present disclosure, and switch 80" may be placed in various configurations relative to the lever 24.

Figure 9:
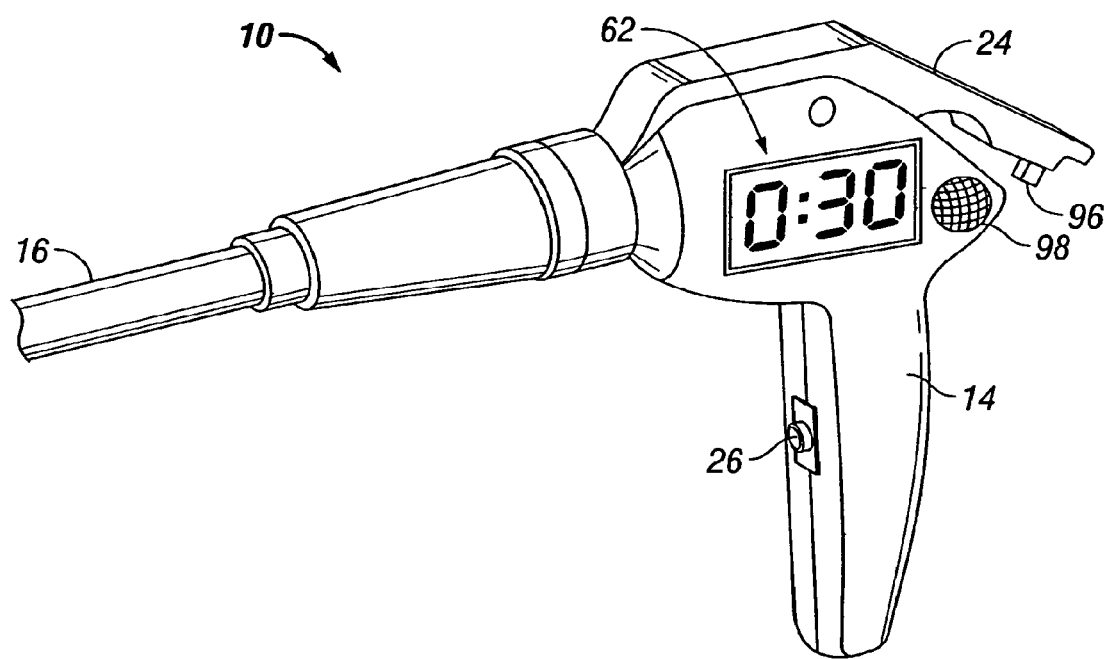
FIG. 9 is another perspective view of still another embodiment of the surgical stapler with an audible alarm.

FIG. 9 shows the surgical stapler 10 with a lever 24. The lever 24, shown in the elevated position, controls the clamp or jaws 21, 22, however this arrangement is not limiting and another driving member may control the clamp or jaws 21, 22 such as the motor 66 (FIG. 7). The lever 24 opens and closes the jaws 21, 22 of the clamp to compress the body tissue prior to surgical stapling. The surgical stapler 10 further includes an electrical contact 96 with an electrically conductive member to complete a suitable analog or digital circuit. The electrical contact 96 is in a complementary nesting location of the lever 24 when the lever is in a lowered position or mating with the handle 14. When the lever 24 is lowered from an elevated or raised position to the lowered position or contacting the handle 14, the lever 24 engages the electrical contact 96. The electrical contact may complete a suitable timer circuit of the display 62 when in the lowered position. In this embodiment, the electrical contact 96 commences the display 62. The display 62 may count upwards from zero to a predetermined time limit, or may count down from an ideal predetermined tissue compression time interval. Once the displayed time reaches the predetermined time interval, an audible alarm 98 may sound. The audible alarm 98 provides the surgeon with a cue that the optimal tissue compression time has been reached, and that the firing mechanism should be actuated in order to fire the staple from the staple cartridge 21 to ensure a uniform staple formation.

Figure 10:
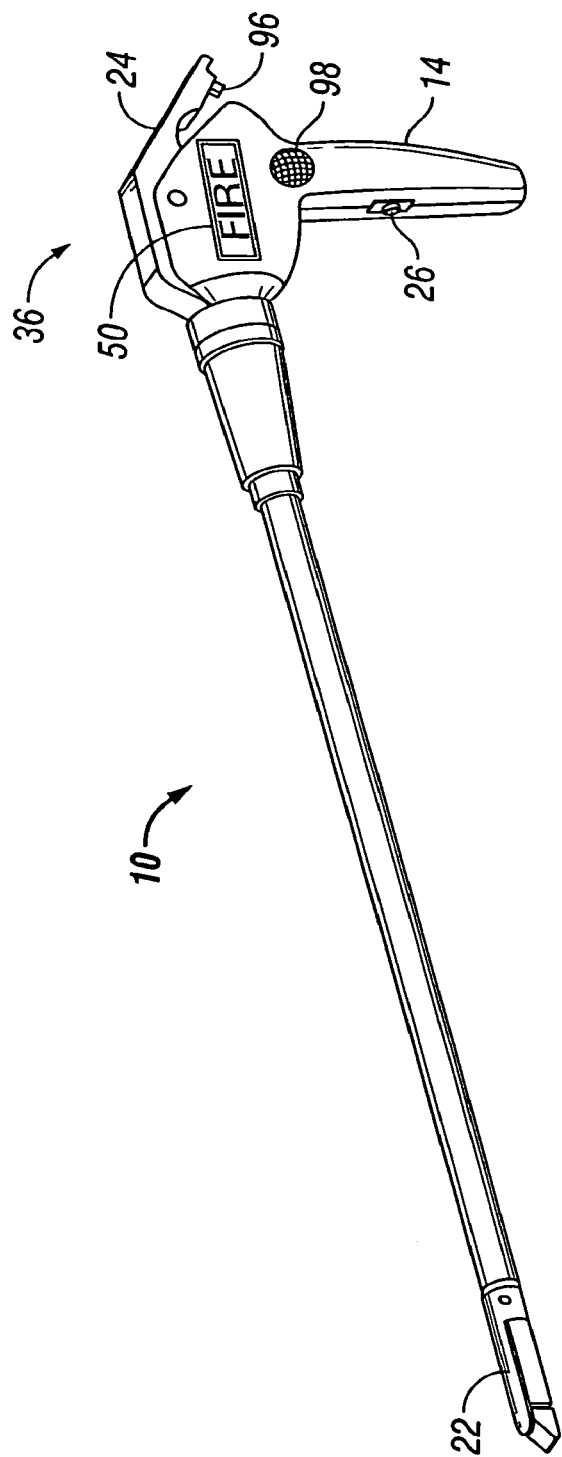
FIG. 10 is still another perspective view of another embodiment of the surgical stapler having the display showing an image.

FIG. 10 illustrates in still another embodiment where the clamp formed by jaws 21, 22 is actuated by lowering the lever 24. Contemporaneously, the timer circuit of the display 62 is activated by the electrical contact 96 on the lever 24. The indicator 36 may be the linear display 50 which indicates a first color to prompt for the actuation of the stapling mechanism 21 by the trigger switch or button 26. The display 50 may then display a second image or illuminate the number of segments corresponding to a travel path of the axial drive screw 74 as shown in FIG. 7. Upon actuation, the second switch 82 outputs a signal to the controller 28. The controller 28 then stops the motor 66, and the controller outputs a control signal to the display 50 to modulate the display from the first color to another second color or from a first image to a second image to indicate that the stapling cartridge 21 has fired. Optionally, the controller 28 may further sound the audible alarm 98 indicating that the stapling cartridge 21 has fired. The alarm may be any sound or audible pattern, including a buzzer, a song, a chirp, a chime or any combinations thereof. Various indicator configurations are possible and within the scope of the present disclosure.

In still another embodiment, the jaws 21, 22 may be actuated by lowering the lever 24. Contemporaneously, the timer circuit of the display 62 is activated by the lever 24. Thereafter, the indicator 36 indicates a first indication to prompt for an actuation of the stapling cartridge 21 by actuating switch 26 after a desired time period elapses. Once the trigger switch 26 is actuated, the controller 28 activates the motor 30. The motor 30 then moves the drive screw 74 as shown in FIG. 7.

Figure 11:
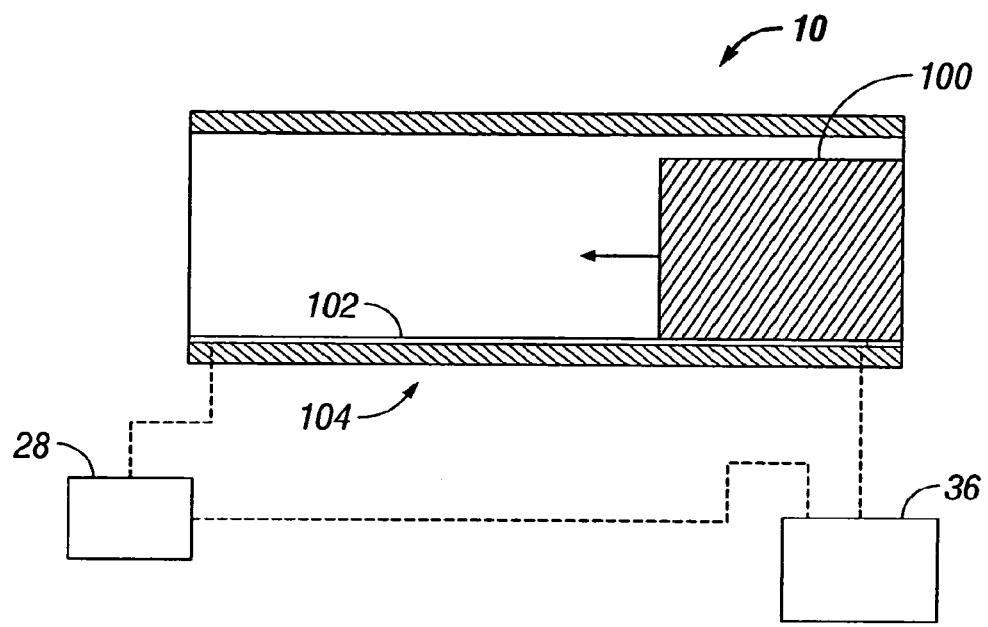
FIG. 11 is a schematic/cross sectional view of a travel path of a drive member through an endoscopic portion of the surgical stapler with a resistor strip.

As the axial drive screw 74 moves in an axial manner, the drive screw (or another plunger 100 connected thereto as shown in FIG. 11) contacts a second member 102. Second member 102 may be any member that modulates based on the motion of the plunger 100 and that can be detected or sensed by another device to provide an indication to the surgeon. The second member 102 may be a resistor strip which changes a resistance along a travel surface 104 of the plunger 100 as the plunger 100 or the axial drive screw 74 traverses along the portion 16 of the surgical stapler 10 (or other suitable travel surface location). The resistor strip 102 is coupled to indicator 36 such that the change in resistance of the resistor strip 102 selectively illuminates each of the lights 40 through 48 to signal an amount of travel by the axial drive screw 74 or the plunger 100 or other suitable drive member.

Alternatively, the resistor strip 102 may be coupled to another indicator 36 such as a linear display 50. The display 50 may illuminate the number of segments 52, 54, 56, 58, and 60 corresponding to a travel of the axial drive screw 74 or the plunger 100 until the axial drive screw actuates the stapler cartridge 21. Upon actuated, the resistor strip 102 outputs a signal to the controller 28 which modulates the operation of the motor 66, and sends another second signal to the display 50 to indicate that the stapling cartridge 21 has fired. The display 50 in response thereto may then display a suitable graphical image, another color, a textual message, or any other indication to indicate to the surgeon that the firing of the stapling cartridge 21 has concluded. Various indicator configurations are possible and within the scope of the present disclosure.

Figure 12:
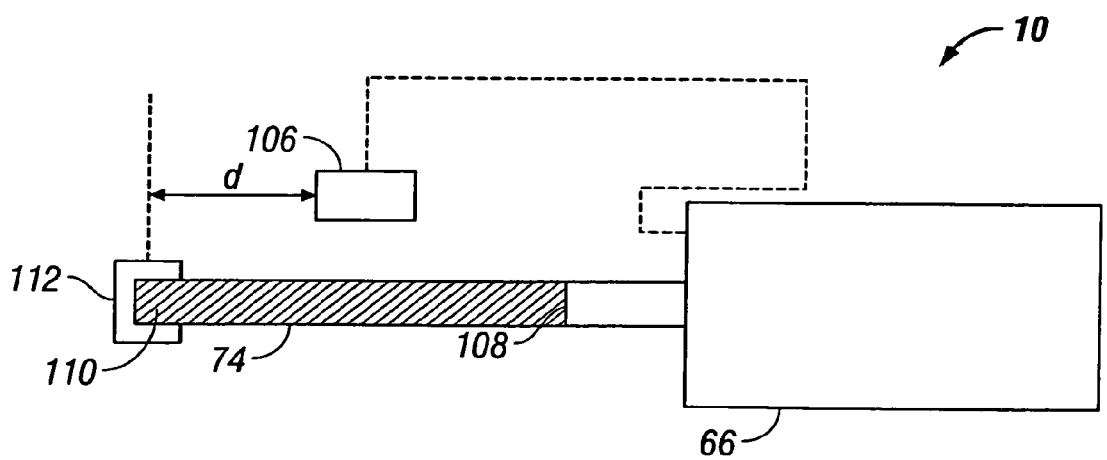
FIG. 12 is a schematic of another embodiment of the surgical stapler having a non-contact sensor.

Referring now to FIG. 12, in yet another embodiment of the present disclosure, the surgical stapler 10 may further include a non-contact sensor 106. The non-contact sensor 106 may optionally be a so-called "Hall effect non-contact sensor" (or alternatively any other non-contact sensor) that is based in part on the physical principle of the Hall effect named after its discoverer E. H. Hall.

For example, end 108 of the axial screw 74 is directly connected, geared to, or offset from the motor 74, and a cap like free end 110 of axial screw 74 contacts the stapler cartridge 21 to actuate the stapler cartridge and to fire the staple as discussed previously. The free end 110 of the drive screw 74 has a magnetic member 112 which connects thereto and which will not become dislodged by a rotation of the drive screw 74. Alternatively, the magnetic member 112 may be disc shaped and simply connect to the free end 110. In one initial orientation, free end 110 and the magnetic member 112 are disposed closely adjacent, or near to the non-contact sensor 106. At this initial orientation, the magnetic member 112 is separated by a first distance "d" from the non-contact sensor 106.

Once the trigger switch or button 26 is actuated, the motor 66 is actuated, and rotates, the drive axial screw 74 to traverse distally to actuate the stapler cartridge 21 as described above. In the second orientation after the motor 66 has been actuated, the magnetic member 112 moves and is a second distance "d" away from the non-contact sensor 106. The second distance is any distance greater than the first distance "d". As the magnetic member 112 moves away from the non-contact sensor 106, the non-contact sensor now located the second distance away from the magnetic field of the magnetic member 112 modulates an operation of the motor 66.

The term "modulation" is defined as modulating amount of voltage received by the motor 66 in a dynamic manner, turning the motor "off" at a desired stroke, changing the motor speed, drive gear reduction of the motor, reduction of the axial drive screw pitch, or a change in the voltage or the current input of the motor, or changing another firing component, a change of the motor components and any combinations thereof. This may thereby slow the operation of the motor 66 to increase an amount of compression time of the body tissues between jaws 21, 22. In another alternative embodiment, the magnetic member 112 may be disposed on a suitable drive piston instead of the drive screw 66. As the drive piston travels away from the non-contact sensor 106, a reduced or modulated amount of voltage may be provided to the motor 66. Still further in another alternative embodiment, the non-contact sensor 106 may be placed at the free end 110 of the drive screw 74 and the magnetic member 112 fixed.

In another embodiment of the present disclosure, the surgical stapler may have a combined drive mechanism. The combined drive mechanism may control both a firing component of the stapling mechanism and a clamping mechanism. The surgical stapler 10 may, upon being actuated, has the drive mechanism advance to commence the clamping using the clamping mechanism and then hold and wait thus providing a predetermined delay. The surgical stapler 10 would then provide an indication to the surgeon/operator once a desired amount of compression is reached. Thereafter, the surgeon/operator would then actuate the drive mechanism after the time delay. The drive mechanism would then fire the staples from the stapling cartridge 21 into the compressed tissues and thus ensure a uniform staple formation. The surgical stapler 10 thus provides a time delay prior to stapling to ensure tissue compression.

Although being shown as an endoscopic surgical stapler, the present drive system may be used with any surgical stapling device known in the art, such as endoscopic surgical stapling devices, a pulmonary stapling device, a GIA surgical stapling devices, an endo-GIA stapling device, a TA surgical stapling device and any other stapler device for surgery know in the art. The present disclosure may also be used with a single drive surgical stapler that drives both the clamp and the stapling device. The present disclosure may be incorporated into a device that approximates and then fires such as with a TA surgical stapling device or with a surgical stapler without any such approximation of tissue.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A powered surgical stapler comprising:
    a handle;
    an endoscopic portion extending distally from the handle and defining a first longitudinal axis;
    a drive motor disposed at least partially within the housing;
    a firing drive screw disposed in mechanical cooperation with the drive motor, the firing drive screw including a first indicator end and a second indicator end;
    a position calculator for determining the linear position of the firing drive screw, the position calculator coupled to at least one linear displacement sensor disposed adjacent to the firing drive screw and configured to detect linear movement of the firing drive screw; and
    a speed calculator for determining at least one of a linear speed of the firing drive screw and rotational speed of the drive motor.

2. A powered surgical stapler according to claim 1, wherein the at last one linear displacement sensor comprises:
    a shaft start position sensor configured to signal the position calculator when the first indicator end interfaces therewith, wherein position of the first indicator end denotes commencement of the firing drive shaft being moved; and
    a clamp position sensor configured to signal the position calculator when the second indicator end interfaces therewith, wherein position of the second indicator end denotes clamping of a fastening assembly.

3. A powered surgical stapler according to claim 1, wherein at least a portion of the firing drive shaft is magnetized or the firing drive shaft includes a magnetic material disposed therein, and the at least one linear displacement sensor is configured to detect variations in the magnetic field corresponding to movement of the firing drive shaft.

4. A powered surgical stapler according to claim 3, wherein the at least one linear displacement sensor is selected from the group consisting of a ferromagnetic sensor and a Hall Effect sensor.

5. A powered surgical stapler according to claim 1, wherein the linear displacement sensor is selected from the group consisting of a potentiometer and a rheostat and the firing rod includes a contact in electromechanical contact with the linear displacement sensors, wherein linear displacement sensor is configured to detect movement of the firing drive shaft based on a change of at least one electrical property thereof.

6. A powered surgical stapler according to claim 1, wherein the speed calculator is coupled to the linear displacement sensor, the speed calculator being configured to determine the linear speed of the firing drive shaft based on rate of change of displacement thereof.

7. A powered surgical stapler according to claim 1, wherein the speed calculator is coupled to a rotation speed detecting apparatus having at least one encoder for transmitting pulses corresponding to speed of rotation of the drive motor.

8. A powered surgical stapler according to claim 1, further comprising a voltage sensor connected to the drive motor which measures back electromotive force thereof, the speed calculator being coupled to the voltage sensor and being configured to determine at least one of a linear speed of the firing drive shaft and rotational speed of the drive motor based on the measured electromotive force.

9. A powered surgical stapler according to claim 1, wherein the speed calculator is configured to compare the linear speed of the firing drive shaft and the rotational speed of the drive motor to determine whether rotation of the drive motor is being sufficiently translated to the firing drive shaft.

10. A powered surgical stapler according to claim 1, wherein the position calculator and the speed calculator are coupled to a control system which includes a microcontroller.

* * * * *